United States Patent
Kovarik et al.

(12)

(10) Patent No.: US 9,730,967 B2
(45) Date of Patent: *Aug. 15, 2017

(54) METHOD AND SYSTEM FOR TREATING CANCER CACHEXIA

(71) Applicants: Katherine Rose Kovarik, Englewood, CO (US); Joseph E. Kovarik, Englewood, CO (US)

(72) Inventors: Katherine Rose Kovarik, Englewood, CO (US); Joseph E. Kovarik, Englewood, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 15/437,976

(22) Filed: Feb. 21, 2017

(65) Prior Publication Data

US 2017/0173085 A1    Jun. 22, 2017

Related U.S. Application Data

(63) Continuation-in-part of application No. 15/228,454, filed on Aug. 4, 2016, now Pat. No. 9,585,920, which is a continuation-in-part of application No. 14/954,074, filed on Nov. 30, 2015, now Pat. No. 9,457,077, which is a continuation-in-part of application No. 14/574,517, filed on Dec. 18, 2014, now Pat. No. 9,408,880, application No. 15/437,976, which is a continuation-in-part of application No. 15/403,823, filed on Jan. 11, 2017, and a continuation-in-part of application No. 15/392,173, filed on Dec. 28, 2016, and a continuation-in-part of application No. 15/395,419, filed on Dec. 30, 2016, and a continuation-in-part of application No. 15/342,642, filed on Nov. 3, 2016, and a continuation-in-part of application No. 15/200,210, filed on Jul. 1, 2016, which is a continuation-in-part of application No. 14/283,459, filed on May 21, 2014, now Pat. No. 9,387,168, application No. 15/437,976, which is a continuation-in-part of application No. 15/378,425, filed on Dec. 14, 2016, which is a continuation of application No. 14/752,192, filed on Jun. 26, 2015, now Pat. No. 9,549,842, which is a continuation-in-part of application No. 14/225,503, filed on Mar. 26, 2014, now Pat. No. 9,445,936, which is a continuation of application No. 13/367,052, filed on Feb. 6, 2012, now Pat. No. 8,701,671, application No. 15/437,976, which is a continuation-in-part of application No. 15/385,278, filed on Dec. 20, 2016, and a continuation-in-part of application No. 15/384,716, filed on Dec. 20, 2016.

(Continued)

(51) Int. Cl.

| | | |
|---|---|---|
| A61K 35/74 | (2015.01) | |
| A61K 31/58 | (2006.01) | |
| A61K 31/436 | (2006.01) | |
| A61K 31/40 | (2006.01) | |
| A61K 31/505 | (2006.01) | |
| A61K 31/366 | (2006.01) | |
| A61K 38/17 | (2006.01) | |
| A61K 38/46 | (2006.01) | |
| A61K 35/00 | (2006.01) | |

(52) U.S. Cl.
CPC ........... *A61K 35/74* (2013.01); *A61K 31/366* (2013.01); *A61K 31/40* (2013.01); *A61K 31/436* (2013.01); *A61K 31/505* (2013.01); *A61K 31/58* (2013.01); *A61K 38/1758* (2013.01); *A61K 38/465* (2013.01); *C12Y 301/03048* (2013.01); *A61K 2035/11* (2013.01)

(58) Field of Classification Search
None
See application file for complete search history.

(56) References Cited

U.S. PATENT DOCUMENTS

| 3,178,341 A | 4/1965 | Hamill et al. |
|---|---|---|
| 4,568,639 A | 2/1986 | Lew |

(Continued)

FOREIGN PATENT DOCUMENTS

| WO | WO 2011/020780 | 2/2011 |
|---|---|---|
| WO | WO 2013/026000 | 2/2013 |

(Continued)

OTHER PUBLICATIONS

Hennessy et al. (Antimicrob. Agents Chemother. doi:10.1128/AAC.00192-16, Jun. 2016).*

(Continued)

*Primary Examiner* — Brian J Gangle
(74) *Attorney, Agent, or Firm* — Sheridan Ross P.C.

(57) ABSTRACT

Various embodiments of the present invention are directed to the field of Oncology, and in particular embodiments directed to a method of ameliorating, treating, or preventing a malignancy in a human subject wherein the steps of the method assist or boost the immune system in eradicating cancerous cells. In certain embodiments, administration of beneficial bacteria to an individual's microbiome that have been modified so as to produce effective amounts of desired compositions, compounds, agents, e.g. tomatidine, p53 protein, statins, etc., is employed to address cancerous conditions. In several embodiments, the administration of such beneficial bacteria and microbes to an individual's microbiome invokes either an active (or a passive) immune response to destroy, weaken or render less invasive certain cancerous cells, and preferably maintains muscle tissue to combat cancer cachexia.

7 Claims, No Drawings

Related U.S. Application Data

(60) Provisional application No. 62/072,476, filed on Oct. 30, 2014, provisional application No. 62/053,926, filed on Sep. 23, 2014, provisional application No. 62/014,855, filed on Jun. 20, 2014, provisional application No. 61/919,297, filed on Dec. 20, 2013, provisional application No. 62/296,186, filed on Feb. 17, 2016, provisional application No. 62/275,341, filed on Jan. 6, 2016, provisional application No. 62/274,550, filed on Jan. 4, 2016, provisional application No. 62/260,906, filed on Nov. 30, 2015, provisional application No. 61/556,023, filed on Nov. 4, 2011, provisional application No. 61/439,652, filed on Feb. 4, 2011, provisional application No. 62/387,404, filed on Dec. 24, 2015, provisional application No. 62/387,405, filed on Dec. 24, 2015.

(56) References Cited

U.S. PATENT DOCUMENTS

| | | |
|---|---|---|
| 4,687,841 A | 8/1987 | Spilburg et al. |
| 4,720,486 A | 1/1988 | Spilburg et al. |
| 4,995,555 A | 2/1991 | Woodruff |
| 5,277,877 A | 1/1994 | Jeffrey et al. |
| 5,614,501 A | 3/1997 | Richards |
| 6,287,610 B1 | 9/2001 | Bowling et al. |
| 6,569,474 B2 | 5/2003 | Clayton et al. |
| 6,722,577 B2 | 4/2004 | Dobyns, III |
| 7,353,194 B1 | 4/2008 | Kerker et al. |
| 7,540,432 B2 | 6/2009 | Majerowski et al. |
| 7,862,808 B2 | 1/2011 | Isolauri et al. |
| 8,030,457 B2 | 10/2011 | Jackson et al. |
| 8,034,601 B2 | 10/2011 | Boileau et al. |
| 8,034,606 B2 | 10/2011 | Park et al. |
| 8,110,215 B2 | 2/2012 | Koenig et al. |
| 8,197,872 B2 | 6/2012 | Mills et al. |
| 8,349,313 B2 | 1/2013 | Smith et al. |
| 8,357,368 B2 | 1/2013 | Dudek et al. |
| 8,362,206 B2 | 1/2013 | Wallach et al. |
| 8,420,074 B2 | 4/2013 | Rehberger et al. |
| 8,454,729 B2 | 6/2013 | Mittelmark et al. |
| 8,496,914 B2 | 7/2013 | Bonfiglio |
| 8,585,588 B2 | 11/2013 | Kovarik et al. |
| 8,591,412 B2 | 11/2013 | Kovarik et al. |
| 8,701,671 B2 | 4/2014 | Kovarik |
| 8,829,165 B2 | 9/2014 | Jackson et al. |
| 8,859,741 B2 | 10/2014 | Jackson et al. |
| 8,945,839 B2 | 2/2015 | Zhang |
| 9,010,340 B2 | 4/2015 | Kovarik et al. |
| 9,011,834 B1 | 4/2015 | McKenzie et al. |
| 9,044,420 B2 | 6/2015 | Dubensky, Jr. et al. |
| 9,045,547 B2 | 6/2015 | Jackson et al. |
| 9,254,295 B2 | 2/2016 | Adams et al. |
| 9,295,682 B2 | 3/2016 | Nunes |
| 9,387,168 B2 | 7/2016 | Barreca et al. |
| 9,408,880 B2 | 8/2016 | Kovarik et al. |
| 9,445,936 B2 | 9/2016 | Kovarik |
| 9,457,077 B2 | 10/2016 | Kovarik et al. |
| 9,549,842 B2 | 1/2017 | Kovarik |
| 2003/0206995 A1 | 11/2003 | Bowling et al. |
| 2004/0053352 A1 | 3/2004 | Ouyang et al. |
| 2004/0115223 A1 | 6/2004 | Follansbee |
| 2004/0142463 A1 | 7/2004 | Walker et al. |
| 2004/0166501 A1 | 8/2004 | Azimzai et al. |
| 2005/0118655 A1 | 6/2005 | Weinstock et al. |
| 2006/0252087 A1 | 11/2006 | Tang et al. |
| 2007/0054008 A1 | 3/2007 | Clayton et al. |
| 2007/0057086 A1 | 3/2007 | Van Kippersluis |
| 2007/0059718 A1 | 3/2007 | Toner et al. |
| 2007/0059774 A1 | 3/2007 | Grisham et al. |
| 2007/0063026 A1 | 3/2007 | Mamaropolos et al. |
| 2007/0087020 A1 | 4/2007 | O'Connor |
| 2007/0123448 A1 | 5/2007 | Kaplan et al. |
| 2007/0207955 A1 | 9/2007 | Tanihara et al. |
| 2007/0231923 A1 | 10/2007 | Cumberland et al. |
| 2008/0112983 A1 | 5/2008 | Bufe et al. |
| 2008/0305089 A1 | 12/2008 | Bufe et al. |
| 2009/0205083 A1 | 8/2009 | Gupta et al. |
| 2010/0029832 A1 | 2/2010 | Pinnavaia et al. |
| 2010/0260720 A1 | 10/2010 | Sprenger |
| 2012/0029832 A1 | 2/2012 | Dodgson |
| 2012/0039806 A1 | 2/2012 | Lahoud et al. |
| 2012/0128597 A1 | 5/2012 | Peters et al. |
| 2012/0142548 A1 | 6/2012 | Corsi et al. |
| 2012/0276143 A1 | 11/2012 | O'Mahony et al. |
| 2012/0276525 A1 | 11/2012 | Kovarik et al. |
| 2013/0059815 A1 | 3/2013 | Fournell et al. |
| 2013/0157876 A1 | 6/2013 | Lynch et al. |
| 2013/0225440 A1 | 8/2013 | Friedman et al. |
| 2013/0259834 A1 | 10/2013 | Klaenhammer et al. |
| 2013/0315869 A1 | 11/2013 | Qimron et al. |
| 2013/0323025 A1 | 12/2013 | Crawford et al. |
| 2013/0323100 A1 | 12/2013 | Poulton et al. |
| 2013/0326645 A1 | 12/2013 | Cost et al. |
| 2013/0330215 A1 | 12/2013 | Li |
| 2014/0030332 A1 | 1/2014 | Baron et al. |
| 2014/0044677 A1 | 2/2014 | Qvit-Raz et al. |
| 2014/0045744 A1 | 2/2014 | Gordon |
| 2014/0066817 A1 | 3/2014 | Kovarik et al. |
| 2014/0068797 A1 | 3/2014 | Doudna et al. |
| 2014/0154290 A1 | 6/2014 | Peters et al. |
| 2014/0255351 A1 | 9/2014 | Berstad et al. |
| 2014/0349405 A1 | 11/2014 | Sontheimer et al. |
| 2014/0363441 A1 | 12/2014 | Grandea, III et al. |
| 2014/0364460 A1 | 12/2014 | Freed-Pastor et al. |
| 2014/0377278 A1 | 12/2014 | Elinav et al. |
| 2015/0004130 A1 | 1/2015 | Faber et al. |
| 2015/0064138 A1 | 3/2015 | Lu et al. |
| 2015/0071957 A1 | 3/2015 | Kelly et al. |
| 2015/0086581 A1 | 3/2015 | Li et al. |
| 2015/0132263 A1 | 5/2015 | Liu et al. |
| 2015/0147371 A1 | 5/2015 | Kovarik et al. |
| 2015/0190435 A1 | 7/2015 | Henn et al. |
| 2015/0252358 A1 | 9/2015 | Maeder et al. |
| 2016/0000754 A1 | 1/2016 | Stamets |
| 2016/0000841 A1 | 1/2016 | Yamamoto et al. |
| 2016/0069921 A1 | 3/2016 | Holmes et al. |
| 2016/0095316 A1 | 4/2016 | Goodman et al. |
| 2016/0151428 A1 | 6/2016 | Bryan |
| 2016/0158294 A1 | 6/2016 | von Maltzahn et al. |
| 2016/0175327 A1 | 6/2016 | Adams et al. |
| 2016/0199424 A1 | 7/2016 | Berry et al. |
| 2016/0206666 A1 | 7/2016 | Falb et al. |
| 2016/0206668 A1 | 7/2016 | Kort et al. |
| 2016/0213702 A1 | 7/2016 | von Maltzahn et al. |
| 2016/0243132 A1 | 8/2016 | Adams et al. |
| 2016/0271106 A1 | 9/2016 | Shi et al. |
| 2016/0354416 A1 | 12/2016 | Gajewski et al. |
| 2017/0020932 A1 | 1/2017 | Cutcliffe et al. |
| 2017/0021011 A1 | 1/2017 | Kovarik et al. |
| 2017/0042924 A1 | 2/2017 | Otsuka et al. |
| 2017/0071986 A1 | 3/2017 | Kovarik et al. |

FOREIGN PATENT DOCUMENTS

| | | |
|---|---|---|
| WO | WO 2013/107750 | 7/2013 |
| WO | WO 2014/103488 | 7/2014 |
| WO | WO 2015/069682 | 5/2015 |

OTHER PUBLICATIONS

U.S. Appl. No. 15/200,210, Barreca et al.
U.S. Appl. No. 15/378,425, Kovarik et al.
U.S. Appl. No. 15/384,716, Kovarik et al.
U.S. Appl. No. 15/385,278, Kovarik et al.
U.S. Appl. No. 15/392,173, Kovarik.
U.S. Appl. No. 15/395,419, Kovarik.
U.S. Appl. No. 15/403,823, Kovarik.
Auerbach et al., "Angiogenesis assays: Problems and pitfalls," Cancer and Metastasis Reviews, 2000, vol. 19, pp. 167-172.
Gura, "Systems for Identifying New Drugs Are Often Faulty," Science, 1997, vol. 278(5340), pp. 1041-1042, 5 pages.

(56) References Cited

OTHER PUBLICATIONS

Jain, "Barriers to Drug Delivery in Solid Tumors," Scientific American, 1994, pp. 58-65.
Kilkkinen et al., "Use of antimicrobials and risk of type 1 diabetes in a population-based mother-child cohort," Diabetologia, 2006, vol. 49, pp. 66-70.
Kimoto et al., "New Lactococcus Strain with Immunomodulatory Activity: Enhancement of Th1-Type Immune Response," Microbiol. Immunol., 2004, vol. 48(2), pp. 75-82.
Norton et al., "The immune response to Lactococcus lactis: Implications for its use as a vaccine delivery vehicle," FEMS Microbiology Letters, 1994, vol. 120(3), pp. 249-256, abstract only, 2 page.
Repa et al., "Mucosal co-application of lactic acid bacteria and allergen induces counter-regulatory immune responses in a murine model of birch pollen allergy," Vaccine, 2003, vol. 22(1), pp. 87-95, abstract only, 1 page.
Sporn et al., "Chemoprevention of Cancer," Carcinogenesis, 2000, vol. 21(3), pp. 525-530.
Zhao et al., Microbiome-generated amyloid and potential impact on amyloidogenesis in Alzheimer's disease (AD), Journal of Nature and Science, 2015, vol. 1(7), pp. 1-5.
Official Action for U.S. Appl. No. 14/574,517, dated Jan. 6, 2016, 13 pages.
Notice of Allowance for U.S. Appl. No. 14/574,517, dated Apr. 15, 2016, 8 pages.
Official Action for U.S. Appl. No. 14/954,074, dated Jun. 30, 2016, 4 pages.
Notice of Allowance for U.S. Appl. No. 14/954,074, dated Jul. 20, 2016, 7 pages.
Official Action for U.S. Appl. No. 15/270,034, dated Apr. 6, 2017, 5 pages.
Official Action for U.S. Appl. No. 15/228,454, dated Sep. 23, 2016, 13 pages.
Notice of Allowance for U.S. Appl. No. 15/228,454, dated Jan. 23, 2017, 7 pages.

\* cited by examiner

METHOD AND SYSTEM FOR TREATING CANCER CACHEXIA

RELATED APPLICATIONS

This application is a continuation-in-part application of U.S. patent application Ser. No. 15/228,454, filed Aug. 4, 2016 (now issued U.S. Pat. No. 9,585,920, issued Mar. 7, 2017), which is a continuation-in-part application of U.S. patent application Ser. No. 14/954,074, filed on Nov. 30, 2015 (now issued U.S. Pat. No. 9,457,077, issued Oct. 4, 2016), which is a continuation-in-part application of U.S. patent application Ser. No. 14/574,517, filed on Dec. 18, 2014 (now issued U.S. Pat. No. 9,408,880, issued Aug. 9, 2016), which is a non-provisional of U.S. Provisional Patent Application No. 62/072,476, filed on Oct. 30, 2014; U.S. Provisional Patent Application No. 62/053,926, filed on Sep. 23, 2014; U.S. Provisional Patent Application No. 62/014,855, filed on Jun. 20, 2014; and U.S. Provisional Application No. 61/919,297, filed on Dec. 20, 2013.

This application is also a continuation-in-part application of U.S. patent application Ser. No. 15/403,823, filed Jan. 11, 2017, which is a non-provisional application of 62/296,186, filed Feb. 17, 2016.

This application is also a continuation-in-part application of U.S. patent application Ser. No. 15/392,173, filed Dec. 28, 2016, which is a non-provisional application of 62/275,341, filed Jan. 6, 2016.

This application is also a continuation-in-part application of U.S. patent application Ser. No. 15/395,419, filed Dec. 30, 2016, which is a non-provisional application of 62/274,550 filed Jan. 4, 2016.

This application is also a continuation-in-part application of U.S. patent application Ser. No. 15/342,642, filed Nov. 3, 2016, which is a non-provisional application 62/260,906 filed Nov. 30, 2015.

This application is also a continuation-in-part application of U.S. patent application Ser. No. 15/200,210, filed Jul. 1, 2016, which is a continuation-in-part application of U.S. patent application Ser. No. 14/283,459, filed May 21, 2014 (now issued U.S. Pat. No. 9,387,168, issued Jul. 12, 2016).

This application is a continuation-in-part application of U.S. patent application Ser. No. 15/378,425, filed Dec. 14, 2016, which is a continuation of U.S. patent application Ser. No. 14/752,192, filed on Jun. 26, 2015, (now issued U.S. Pat. No. 9,549,842, issued Jan. 24, 2017) which is a continuation-in-part application of U.S. patent application Ser. No. 14/225,503, filed on Mar. 26, 2014, (now issued U.S. Pat. No. 9,445,936, issued Sep. 20, 2016) which is a continuation of U.S. patent application Ser. No. 13/367,052, filed Feb. 6, 2012 (now issued U.S. Pat. No. 8,701,671, issued Apr. 22, 2014), which is a non-provisional of U.S. Provisional Patent Application No. 61/556,023, filed on Nov. 4, 2011 and U.S. Provisional Patent Application No. 61/439,652, filed Feb. 4, 2011.

This application is also a continuation-in-part application of U.S. patent application Ser. No. 15/385,278, filed Dec. 20, 2016, which is a non-provisional application of U.S. Provisional Patent Application No. 62/387,404, filed Dec. 24, 2015.

This application is also a continuation-in-part application of U.S. patent application Ser. No. 15/384,716, filed Dec. 20, 2016, which is a non-provisional application and U.S. Provisional Patent Application No. 62/387,405, filed Dec. 24, 2015.

FIELD OF THE INVENTION

A method and system for treating cancer cachexia employing CRISPR-Cas technology to modify an individual's microbiome, and in particular to a method and system designed to produce one of tomatidine, statins, and/or p53 in an individual's microbiome in order to combat cancer cachexia.

BACKGROUND OF THE INVENTION

There are over 200 different known cancers that afflict human beings. Cancer causes millions of deaths a year worldwide and rates are also rising as more people live to an older age and urbanization causes more stress. It is anticipated that one in eight people currently alive will eventually die of cancer. Cancer manifests itself in a wide variety of forms, characterized by different degrees of invasiveness and aggressiveness. Malignant tumors are the second leading cause of death in the United States, after heart disease.

Cachexia is a positive risk factor for death, meaning that if a patient has cachexia, the chance of death from the underlying condition is increased dramatically. Skeletal muscle atrophy is a nearly universal consequence of cancer. Cachexia is considered the immediate cause of death of a large proportion of cancer patients, ranging from 22% to 40% of cancer patients. The pathogenesis of cancer cachexia is poorly understood. It is believed that multiple biologic pathways are involved, including proinflammatory cytokines and tumor-specific factors such as proteolysis-inducing factor. Muscle atrophy is believed to occur by a change in the normal balance between protein synthesis and protein degradation. During atrophy, there is a down-regulation of protein synthesis pathways and an activation of protein breakdown pathways. Only limited treatment options exist for patients with clinical cancer cachexia. Current treatment strategies involve attempting to improve an individual's appetite using appetite stimulants and protein supplementation to provide the individual with required nutrients.

The reversal of cancer cachexia and muscle wasting leads to prolonged survival, and with the ability to retain muscle mass and strength, it is believed that various forms of cancer treatment may be more effective, if only due to the fact that the cancer victim may be able to withstand the rigors of the various cancer treatments involved. There is presently, however, an absence of effective medical therapies to prevent or reverse skeletal muscle atrophy, and especially therapies that involve reliance on a modification of a patient's microbiome. Current treatment recommendations to address skeletal muscle atrophy (e.g. physical rehabilitation, nutritional optimization, and treatment of underlying disease) are often ineffective and/or unfeasible and at present, a pharmacologic therapy does not exist. Thus, a treatment for skeletal muscle atrophy associated with cancer represents a very large unmet medical need.

Cachexia is seen in the late stages of almost every major chronic illness, affecting 16-42% of people with heart failure, 30% of those with chronic obstructive pulmonary disease and up to 60% of people with kidney disease. Cachexia was overlooked for many years, with doctors directing their attention to the primary illness instead. Many, however, now view cachexia as a distinct, treatable condition. Basic research has revealed how it is driven by inflammation and metabolic imbalances. Treating cachexia may possibly give patients the strength to withstand chemotherapy or surgery. A key mechanism underlying cachexia is the increased breakdown of muscle protein, along with dampened protein synthesis, which leads to overall muscle loss. Certain genes are active in atrophying muscles, including genes encoding enzymes called E3 ubiquitin ligases, which tag proteins for destruction in the cell. Muscle cells seem to make more of these ligases when hit with certain inflammatory signals from tumors or from immune cells responding to cancer or other illness.

In the US, bladder cancer is the fourth most common type of cancer in men and the ninth most common cancer in women. Non-muscle invasive bladder cancer (NMIBC) begins and stays in the cells lining the bladder without growing into the deeper main muscle layer of the bladder, and accounts for the majority (70-80%) of patients diagnosed with bladder cancer. Bladder cancer has the highest recurrence rate of any malignancy. Although NMIBC is a relatively benign disease, it recurs in 50-70% of patients, of which 10-20% eventually progress to high-grade muscle-invasive disease. More than 1 million patients in the US and Europe are estimated to be affected by the disease.

The clinical management of bladder cancer has not changed significantly in several decades, with intravesical *bacillus* Calmette-Guérin immunotherapy being a mainstay for high-risk nonmuscle invasive bladder cancer since the late 1970s/early 1980s. Bacille Calmette-Guerin strains are currently used as commercial vaccines, with descendants of the original *M. bovis* isolate being passaged in vitro through hundreds of cycles. Following surgical treatment and depending on its stage, non-muscle invasive bladder cancer (NMIBC) can be controlled by immunotherapy using the *Bacillus* Calmette Guerin (BCG) vaccine instilled repeatedly in the bladder, usually as a six-week course followed by yearly maintenance therapy. The application of the BCG vaccine in this context is a first line therapy and generally regarded as the oldest and to date most successful immunotherapy of cancer. The anti-tumor effect of BCG is not fully understood, but involves infection of urothelial or bladder cancer cells and induction of both nonspecific inflammatory as well as specific anti-tumoral responses. NMIBC is typically treated with intravesicular BCG, which elicits a nonspecific local immune response against the tumor cells. BCG also elicits a nonspecific massive local inflammatory reaction in the bladder wall, and elevated appearance of cytokines can be detected in the urine of BCG-treated patients. BCG is internalized by antigen-presenting cells, such as macrophages, but also by urothelial tumor cells, which result in an altered gene expression of these cells.

The majority of tumors harbor p53 mutants. As the "guardian of the genome," p53 is arguably one of the most important tumor suppressors that controls the regulation and expression of many genes that mediate cell cycle arrest, DNA repair and apoptosis. Under physiological conditions, newly synthesized p53 quickly undergoes ubiquitination and degradation. The p53 tumor suppressor protein plays critical roles in preventing malignant transformation by inducing cell growth arrest or apoptosis. Normally, p53 is inactive in the cell and its levels are low. In response to cellular stress such as DNA damage, p53 levels increase dramatically and it becomes activated through multiple post-translation modifications. Although the induction of p53 is partly due to its stabilization through interaction with the ubiquitin ligase MDM2, it is now clear that newly synthesized p53 also contributes to its accumulation. The induction of p53 following DNA damage is accompanied by increased association between eIF-4E, a protein translation initiator that binds to 5'-cap of eukaryotic mRNA, and its inhibitory protein 4E-BP1. This indicates a decrease in cap-dependent translation following DNA damage. An internal ribosomal entry site (IRES) at the 5'-untranslated region (UTR) of the p53 mRNA can recruit the 40S ribosomal subunit independent of the eIF-4E protein in response to DNA damage and other cellular stress. The presence of the IRES sequence is found in the p53 mRNA. It is believed that p53 down-regulates the activity of enablers such as FGF13.

Despite massive research efforts and the very impressive progress made over the past several decades, full molecular understanding of cancer and cachexia still remains a major challenge to the biomedical community. There exists a long felt but unsolved need for a simple, relatively inexpensive, effective treatment of muscle atrophy associated with a host of different types of cancer and other diseases. The present invention addresses this need in a manner heretofore unappreciated or at least unrecognized by those in the relevant art.

SUMMARY OF THE INVENTION

As described in more detail herein, one aspect of the present invention involves the use of a natural small molecule derived from tomato plants, tomatidine, which is believed to cause cell growth, especially in skeletal muscle tissue. Tomatidine is an inhibitor of muscle atrophy and thus has a use as a therapeutic agent for skeletal muscle atrophy. Tomatidine is a steroidal alkaloid and the aglycone of alpha-tomatine, an abundant glycoalkaloid in tomato plants that mediates plant defense against fungi, bacteria, viruses and predatory insects. When consumed by animals, alpha-tomatine is hydrolyzed by stomach acid and intestinal bacteria to tomatidine, which is absorbed by the gut. Tomatidine is believed to have an anti-atrophic (anabolic) effect in skeletal muscle and possesses anti-hyperlipidemic and anti-atherosclerotic effects without evidence of toxicity. Tomatidine is significantly more potent than ursolic acid in building muscle tissue and has a different mechanism of action.

One aspect of the present invention is directed to the provision to individuals in need thereof of bacteria that have been modified to produce effective amounts of tomatidine to address the muscle atrophy associated with various cancers and diseases. In one embodiment, DNA encoding tomatidine or its analogs is inserted into the genome of one or more bacterial species by employing CRISPR-Cas or Cf11 systems, such that an individual can orally take a pill containing such modified bacteria (preferably bacteria of the same species as presently reside in the individual's gut microbiome) and in such a manner, administer tomatidine to the individual in a manner that does not require injections or the taking of traditional pharmaceutical formulations containing tomatidine. In such a manner, the production by such bacteria inside the individual provides a more natural way for tomatidine to be provided to those in need of its extraordinary abilities to foster the retention of muscle mass in the individual. The ability to further modify the populations of bacteria inside an individual via the use of particular antibiotics, for example, those that can target the modified species that produce tomatidine, provides a way to control the amount of tomatidine in the individual's body. Tomatidine in this instance, is but one of many examples of how the personal microbiome of an individual can be amended, modified, enhanced and/or changed to adjust the levels and amounts of various compounds, drugs, molecules, etc. that are important in maintaining or restoring health to an individual.

In certain embodiments of the present invention, a method for treating cancer cachexia involves the administering to the microbiome of a subject in need thereof of an effective amount of a bacterial combination that expresses p53 protein and tomatidine, such cancer being for example, one of breast cancer, bladder cancer, kidney cancer, or colorectal cancer. In certain embodiments, the cancer is a metastatic cancer; and the microbiome is one or more of the gut microbiome, the oral microbiome or the skin microbiome. Other embodiments involve mucosally administering to the subject an effective amount of a bacteria that has been modified to express one of tomatidine, statins and/or p53, with the bacteria selected from the group consisting of *Streptococcus, Actinomyces, Veillonella, Fusobacterium, Porphromonas, Prevotella, Treponema, Neisseria, Haemophilus, Eubacteria, Lactobacterium, Capnocytophaga, Eikenella, Leptotrichia, Peptostreptococcus, Bacillus Calmette Guerin, Staphylococcus*, and *Propionibacterium*. Still other embodiments include the provision of *Streptomyces hygroscopicus* in an amount effective to produce therapeutically effective amounts of rapamycin to the subject. It should be appreciated that a therapeutically effective amount is preferably an amount sufficient to elicit any of the listed effects of natural tomatidine and p53, for example, including, but not limited to, the power to treat cancer cachexia in a fashion demonstrated by a result indicating that there is evidence of the maintenance of muscle mass in the individual treated. In certain preferred embodiments, the mucosal administration is oral administration and the subject individual maintains or increases muscle mass. In most preferred embodiments, the bacterial composition has been modified via a CRISPR-Cas or Cfl1 system to express tomatidine, and in other embodiments, produces both tomatidine and p53 protein. Other embodiments include a bacterial composition that includes one of a *Chlamydia* species, *Shigella flexneri, Mycoplasma bacteria*, and/or *H. pylori*.

The TP53 gene, which encodes the p53 protein, is the most frequent target for mutation in tumors. In response to a number of stressors, p53 becomes activated to promote cell cycle arrest, apoptosis or senescence thereby suppressing tumor growth and also plays many additional roles including regulating cellular metabolism. Unlike most tumor suppressor genes, which are predominantly inactivated as a result of deletion or truncation, the majority of mutations in TP53 are missense mutations. In contrast to wild-type p53, which under unstressed conditions is a very short-lived protein, missense mutations lead to the production of full-length p53 protein with a prolonged half-life. While many tumor-derived mutant forms of p53 can exert a dominant-negative effect on the remaining wild-type allele, serving to abrogate the ability of wild-type p53 to inhibit cellular transformation, the end result is that the wild-type version of p53 is lost and the mutant form is retained, with cancer and cachexia resulting. There is substantial evidence that certain mutants of p53 can exert oncogenic, or gain-of-function, activity independent of their effects on wild-type p53. There is a great need for methods of treating cancer having mutated p53 protein and TP53. Certain embodiments of the present invention address such need by providing methods and systems whereby the oncogenic mutant p53 populations are hindered via the provision of agents that block their activities, such as statins, while also providing a new source of wild-type p53 produced by added bacteria to the individual. Enhancing an individual's microbiome with microbes that are also able to produce tomatidine and rapamycin is a further way to combat various disease conditions and to restore health to the individual.

Over 50 percent of human tumors contain mutations in the gene encoding p53, a protein that plays a significant role in early carcinogenesis. Wild-type p53 is a tumor suppressor, but mutant p53 has been shown to exhibit gain-of-function properties as well, causing cancer formation by enabling normally suppressed pathways. One such oncogenic pathway activated by this mutation is the sterol biosynthesis pathway. 3-Hydroxy-3-methylglutaryl CoA reductase inhibitors (statins) have proven therapeutic and demonstrate preventative effects in cardiovascular diseases. Inhibition of this pathway using HMG-CoA Reductase inhibitors, commonly known as statins, forms various aspects of the present invention and provides an entirely new treatment against mutant p53 expressing cancers, especially with respect to the delivery of statins being via microbes administered to individuals. Statins are among the most carefully studied class of drugs in use and are well tolerated with an excellent safety profile. Statins are already FDA approved and widely used for other indications. Statins also have other beneficial anti-inflammatory and immune-modulatory effects.

Various aspects of the present invention involve the confluence of some historically important developments in the biological sciences, including the recognition of the importance of the microbiome, the advent of CRISPR-Cas systems to manipulate various genes and organisms, and the ability to better control the "holy grail" of cancer therapy, namely the use of competently folded p53 protein and the reduction of the actions of mutant p53 on the progression of cancer. With the further acknowledgement of tomatidine as one of the natural plant-derived agents that can have a positive effect on cachexia, especially that associated with cancer, as well as the beneficial effects from the administration of rapamycin via an individual's microbiome, there is presently a new and extraordinary opportunity to advance the long sought but heretofore unfulfilled prospects of effectively treating cancer so as to substantially extend the quality and quantity of life for those suffering therefrom.

Still further aspects of the present invention are directed to the appreciation that cancer and aging appear to be related in many ways, as the ability of cancer to be immortal is a characteristic that if understood, could be applied to the aging of cells, thus providing an ability to combat age related diseases. By understanding how p53 can be administered to cancer tissues to halt cancer progression, while at the same time, stopping the ability of mutated p53 to promote cancer growth, a large step in providing a treatment for cancer is achieved. The further provision of modified microbes administered to an individual's microbiome so as to produce effective amounts of particular agents, such as tomatidine (to forestall muscle atrophy), rapamycin (to address aging issues), etc., is a further benefit that may be achieved, especially given the CRISPR-Cas technologies that easily provide an unprecedented ability to modify microbes in this regard—and without having to genetically engineer human cells in the process of such treatments.

Still other embodiments of the present invention are directed to the employment of anaerobic bacteria to address cancer growth as the biological environment of cancerous tumors and anaerobic bacteria are similar in several respects. Abnormal blood vessels and hypoxic and necrotic regions are universal features of solid tumors. These hypoxic and anoxicmicroenvironments may be targeted by obligatory or facultative anaerobic bacteria, such as *Bifidobacterium, Salmonella, Escherichia, lostridium* and *Listeria*, as well as certain bacteria believed to be involved in the progression of Alzheimer's Disease, namely, *spirochetes*. Some of these bacteria accumulate and actively proliferate within tumors, resulting in much higher increases in the number of bacterial cells in tumor tissues relative to those in normal organ cells and tissues, such as liver and spleen. The use of attenuated bacterial strains to suppress tumor growth forms one aspect of the present invention, and in particular, use of BCG that has been further modified to express particular agents, such as tomatidine, p53, statins, rapamycin, etc. whether in separate bacterial cells or the same bacterial cell, comprises various aspects of the present invention. Such modified bacteria may act by directly suppressing tumor growth directly and/or by activating host immunity, but are effective in achieving improved therapeutic effects. One advantage of various embodiments of the present invention is that instead of having to inject bacteria into a patient's tumor, the administration of agents is achieved preferably via the more organic administration of agents via the bacterial and host cell interactions. Various of the embodiments encompassed herein rely upon approaches that stimulate inflammation, and thus trigger an antitumor immune response by the individual.

Other aspects of certain embodiments of the present invention are directed towards the administration of quercetin, a polyphenol abundant in plants, preferably as it is or in the form of a glycoside. Quercetin may be found in various plants including citrus fruits, onion, buckwheat, and sophora and it is known that it has a wide variety of physiological functions, such as platelet aggregation/adhesion inhibition activities, and vasodilatory activity. In various embodiments of the present invention, quercetin is expressed by cells of an individual's microbiome to elicit anticancer activity and to confer other health benefits. The administration of certain modified bacteria to an individual in various embodiments effectively creates microbial cell factories that, through metabolic engineering of heterologous biosynthetic pathways, turns microbes into a cost effective and more organic way to both produce and administer agents to desired tissues in a person suffering from cancer and other diseases. Using CRISPR-Cas techniques especially, and in view of the guidance provided herein, one of ordinary skill in the art will be able to excise desired genes from plants, bacteria and fungi and have them expressed by microbes that can be administered to an individual's microbiome such that health can be restored to the individual.

In addition, treatments for various types of cancer are desired that relate to the production of competently folded p53 tumor support factor. There has been a long felt but unmet need for a way to inexpensively administer desired amounts of p53 protein to an individual in need thereof. The present invention in several of its aspects addresses this concern, for example, by the expression of p53 by human microbiome bacteria, by the administration of BCG cells transformed to express p53 (as well as statins, rapamycin, tomatidine, quercetin, neoalbaconol, a phosphatase and tensin homolog (PTEN), etc.

Thus, in particular embodiments, the present invention is specifically directed to a method of treating cancer cachexia in a subject in need of such treatment by administering a therapeutically effective amount of a composition comprising *bacillus* calmette-guerin that is adapted to produce tomatidine, wherein the cancer is bladder cancer or alternatively colorectal cancer. The *bacillus* calmette-guerin is preferably modified via a CRISPR-Cas system to produce tomatidine, is even more preferably adapted to also produce rapamycin, and even more preferably adapted to further produce a statin, such as one or more of Mevacor™, Pravachol™, simvastatin, atorvastatin, fluvastatin, lovastatin, pravastatin and rosuvastatin. In still other embodiments, the *bacillus* calmette-guerin is adapted to produce neoalbaconol, and even more preferably, it is further adapted to produce p53. Other embodiments are similar to that described above, but the *bacillus* calmette-guerin is specifically adapted to produce tomatidine and the cancer is colorectal cancer. One will appreciate that similar preferred embodiments include *bacillus* calmette-guerin being further adapted to produce one or more of rapamycin, a statin, a phosphatase and tensin homolog (PTEN), p53 and/or neoalbaconol.

One will appreciate that this Summary of the Invention is not intended to be all encompassing and that the scope of the invention nor its various embodiments, let alone the most important ones, are necessarily encompassed by the above description. One of skill in the art will appreciate that the entire disclosure, as well as the incorporated references, pictures, etc. will provide a basis for the scope of the present invention as it may be claimed now and in future applications. While embodiments of the invention have been illustrated and described, it is not intended that these embodiments illustrate and describe all possible forms of the invention. Rather, the words used in this specification are words of description rather than limitation, and it is understood that various changes may be made without departing from the spirit and scope of the invention.

DETAILED DESCRIPTION OF CERTAIN EMBODIMENTS OF THE INVENTION

The forgotten organ—the human microbiome—comprises a community of microorganisms that colonizes various sites of the human body. Through coevolution of bacteria, archaea and fungi with the human host over thousands of years, a complex host-microbiome relationship emerged in which many functions, including metabolism and immune responses, became codependent. This coupling becomes evident when disruption in the microbiome composition, termed dysbiosis, is mirrored by the development of pathologies in the host. Among the most serious consequences of dysbiosis, is the development of cancer.

In one embodiment, a person is provided with beneficial microbes that are adapted to produce therapeutic amounts of tomatidine to achieve the stimulation of skeletal muscle anabolism, leading to muscle hypertrophy, increased strength and improved exercise capacity. Preferably, tomatidine is produced by such microbes, preferably by a person's gut bacteria, in a manner effective to increase skeletal muscle and to decrease fat of such individual, due to tomatidine's ability to limit the progression of skeletal muscle atrophy.

One aspect of the present invention is directed to the provision to a person, via their oral and/or gut or other microbiomes, of effective amounts of tomatidine that is produced from the microbes in that individual's microbiome such that the microbes promote the growth of larger muscles, but without increasing overall body weight. It will be appreciated that still other aspects of the present invention involve the treatment of obesity (as well as various forms of cancer) by providing certain amounts of tomatidine via a person's microbiome to facilitate muscle mass increases while at the same time, decreasing the amount of fat weight of the individual being administered the tomatidine. While treatment of obesity is one possible application of the present invention, a principal objective is to describe embodiments directed to the abatement of muscle mass loss by those suffering from cancer.

Other aspects of the present invention relate to the reduction of the likelihood of, treatment and/or prevention of cancer by interrupting a microbial carcinogenic pathway, and by enhancing an individual's survival by addressing the muscle atrophy associated with cancer. Various embodiments of the present invention use microbiota modifications to improve the efficacy of existing treatments, and in particular, the provision of tomatidine via the production by a patient's microbiome is one aspect of how to address the treatment and prolonged survival of cancer victims.

Short-chain fatty acid production by commensal bacteria is important in regulating the immune system in the gut. Butyrate plays a direct role in inducing the differentiation of regulatory T cells and suppressing immune responses associated with inflammation. Butyrate is normally produced by microbial fermentation of dietary fiber and plays a central role in maintaining colonic epithelial cell homeostasis and barrier function. Various embodiments described herein promote the production of butyrate via modified microbes administered to an individual, alone or in concert with the various other agents as described herein.

Preferably, the modified bacteria employed in certain embodiments of the present invention are administered orally to a patient in order to deliver the therapeutic directly to the site of inflammation in the gut. The advantage of this approach is that it avoids systemic administration of immunosuppressive drugs and delivers the therapeutic directly to the gastrointestinal tract. The viability and stability of such modified bacteria is preferably enhanced to support the production of such microbes of desired agents, e.g. tomatidine, p53 protein, etc. and by doing so, a method is provided that reduce gut inflammation, enhance gut barrier function, and/or treat autoimmune disorders. Preferably, such modified bacteria are capable of producing therapeutic anti-inflammation and/or gut barrier enhancer molecules, particularly in the presence of reactive nitrogen species, and more preferably the bacteria are functionally silent until they reach an environment containing local RNS, wherein expression of the therapeutic molecule is induced. In certain embodiments, the genetically or CRISPR engineered bacteria are non-pathogenic and may be introduced into the gut in order to reduce gut inflammation and/or enhance gut barrier function. For example, in some embodiments, the bacteria are under the control of a RNS-responsive regulatory region and a corresponding RNS-sensing transcription factor such that a desired product, e.g. butyrate, is produced, which induces the differentiation of regulatory T cells in the gut and/or promotes the barrier function of colonic epithelial cells. Use of such modified bacteria, especially those modified via CRISPR-Cas systems, provides a way to generate a desired therapeutic effect in a manner that lowers the safety issues associated with systemic exposure.

Various embodiments of the present invention are directed to the field of oncology, and in particular, embodiments directed to a method of ameliorating, treating, or preventing a malignancy in a human subject wherein the steps of the method assist or boost the immune system in eradicating cancerous cells. In certain embodiments, the administration of beneficial bacteria to an individual's microbiome is achieved, with such bacteria being modified so as to produce effective amounts of desired compositions, compounds, agents, etc., e.g. tomatidine, p53 protein, etc., to address cancerous conditions. In several embodiments, the administration of such beneficial bacteria and microbes to an individual's microbiome invokes either an active (or a passive) immune response to destroy, weaken or render less invasive certain cancerous cells. Various other embodiments are drawn to the co-administration of biological adjuvants (e.g., interleukins, cytokines, Bacillus Comette-Guerin, monophosphoryl lipid A, etc.) in combination with conventional therapies for treating cancer. In particular, the co-administration of various pre-biotic compositions to enhance and sustain the desired effects of the beneficial modified bacteria forms another aspect of the present invention. In this regard, incorporation by reference of U.S. Patent publication No. 20160213702 to Maltzahn et al. is included as part of the written description of various aspects of the present invention. For example, in view of the fact that the microbiota of humans is complex and varies by individual depending on genetics, age, sex, stress, nutrition and diet, modifying the numbers and species of gut, oral, vaginal and skin microbiota can alter community function and interaction with the host. A number of probiotic bacteria known in the art, as well as some foods considered to be 'prebiotic' that contain substances that promote the growth of certain bacteria and that stimulate beneficial microbiota shifts to improve human health, can be employed in concert with the modified bacteria as described herein to effect desired cancer treatment regimens. For example, the administration of glycans in an amount effective to modulate the abundance of the bacterial taxa can be used to achieve better outcomes for cancer patients.

One application of the present invention is to provide a CRISPR-Cas modified bacteria, such as a lactobacteria or BCG, to a person diagnosed with cancer, so as to facilitate the production of tomatidine in a manner that is effective to preserve muscle mass and function in such individual. Other embodiments include CRISPR-Cas, CasX, CasY, etc. modified bacteria that express levels of tumor suppressor factors, such as p53, in a manner that provides an effective, therapeutic amount to an individual via the production of such factors by one or more of the individual's microbiome (e.g. gut, oral, skin, vaginal, etc.) By having the individual's microbiome responsible for administration of such factors, instead of attempting to administer such factors via more traditional routes, such as injection, pills, etc., it is believed that a better result can be attained in a much more natural fashion. Moreover, in view of the ability to further modify bacteria in various ways to provide desired factors at particular times, or in conjunction with particular agents, it is possible to fine tune the administration of desired factors, such as p53, so as to reduce any under or over production thereof. For example, rendering particular modified bacteria sensitive to a predetermined antibiotic can thus provide a way to reduce the numbers of any given modified bacteria in a manner to control the populations of such bacteria in an individual's microbiome, and hence, control the level of production of factors produced by such bacteria. To comply with written description and enablement requirements, incorporated herein by the following references are the following patent publications: U.S. Patent publication Nos. 20140349405 to Sontheimer; 20140377278 to Elinav; 20140045744 to Gordon; 20130259834 to Klaenhammer; 20130157876 to Lynch; 20120276143 to O'Mahony; 20150064138 to Lu; 20090205083 to Gupta et al.; 20150132263 to Liu; and 20140068797 to Doudna; 8945839 to Zhang; 20140255351 to Berstad et al.; 20150086581 to Li; PCT/US2014/036849 and WO 2013026000 to Bryan; 20160199424 to Berry et al.; 20130326645 to Cost et al.

CRISPR-based genetic editing tools offer an efficient way to manipulate expression levels of multiple genes and to provide a solution towards the "multivariate modular metabolic engineering", to optimize the drug synthesis pathways with modular, multiplex regulation using only a few core proteins (e.g., dCas9) that are guided to specific sequences by guide RNAs.

In still other embodiments of the present invention, modifying bacteria so as to administer them to a person's microbiome is performed in a manner so that particular agents, factors or proteins derived from fungi and mushrooms, are rendered possible, with desired mushroom derived components believed to have anti-cancer characteristics, either alone or when used in conjunction with other agents. In particular, combining the referenced ability to have bacteria within a person produce desired amounts of tomatidine as well as having the same bacteria (or in other embodiments, another bacteria) produce a separate cancer-fighting agent, is one novel aspect of the present invention. In particular, by assessing initially the particular bacterial constituents of an individual's microbiome and then administering to such individual a similar species of microbe, but one which has been modified, preferably via employment of a CRISPR-Cas system, one is able to effectively administer to such individual various desired anti-cancer treatments in a way that is believed to be far less disruptive, efficient and dependable as compared to other routes of administration. The modification of specially designed bacteria that reside in a person's body is believed to alleviate the concerns regarding genetic alteration of the human genome, as what is being modified is a microbiome that is present in a person's body—but is not directly involved in the human genome itself. There are a myriad of ways to combine various triggering factors to turn on or off particular productions of agents, factors or proteins that may be included in such modified microbiome species. The present invention in various embodiments is directed to at least those embodiments where cancer therapeutic agents can be administered by the microbiome of the individual that has cancer so as to effectively treat the cancer and/or remedy the symptoms resulting from the disease.

One aspect of the present invention is directed to the employment and modification of an individual's microbiome to address muscle mass retention and as a corollary thereof, to address the counterpart of obesity by lessening the amount of fat storage by such individual. In certain embodiments, the provision of effective amounts of tomatidine is rendered available to an individual via the inoculation of the individual's microbiome (e.g. oral or gut) by particular bacteria that have been modified to express amounts of tomatidine. Still other embodiments also involve the reduction in the amount of acetate levels in an individual's body, which in turn lowers the amount of insulin the individual will produce, which has the effect of keeping fat cells from storing more energy in the form of fat. The reductions in the amount of acetate available in an individual's body further reduces the amount of the hormone ghrelin, thus reducing the hunger drive of the individual. Thus, the modification of an individual's microbiome influences various aspects of their metabolism in a manner that not only retains and maintains the ability to nurture muscle tissue, but to also reduce obesity by affecting the amount of fat that the body stores. While not bound by theory, it is believed that the gut bacteria of an individual is a substantial source of acetate production. The production of acetate by gut microbes is believed to send signals to the brain of the individual to initiate the production of insulin, conveyed via the vagus nerve. Fine tuning of the amount and type of gut microbes (e.g. via the use of antibiotics to initially reduce the kind and numbers of undesired bacteria, followed by purposeful inoculation of an individual's gut microbiome with modified microbes, e.g. via CRISPR-Cas insertion of particular factors, proteins, etc., such as tomatidine) is an effective way to address not only muscle wasting issues, but also obesity issues of individuals.

While there are many gut bacteria that produce acetate, particular bacteria are preferably selected and even more preferably are modified using CRISPR-Cas systems to address the levels of acetate production once such bacteria are introduced to an individuals' microbiome. Preferably the gut microbiota are members of two bacterial divisions: the *Bacteroidetes* and the *Firmicutes*. The modification of an individual's gut microbiome is directed in a manner such that the typical increase seen in the relative abundance of the *Firmicutes* and a corresponding division-wide decrease in the relative abundance of the *Bacteroidetes* in obese individuals, is addressed. Obese people have more *Firmicutes* and almost 90% less *Bacteroidetes* than the lean people. Preferably, the administration of modified *Bacteroidetes* is achieved to more substantially reflect gut populations in more lean individuals, and by doing so, reducing the amount of acetate produced by the overall gut microbiome. Such a shift in the population of gut microbes to favor *Bacteroidetes* over *Firmicutes*, whether or not coupled with the administration of tomatidine, is one aspect of the present invention's objective of achieving a greater proportion of muscle mass than fat that would otherwise occur in any given individual. In still other embodiments, addressing the acetate production by especially *Firmicutes*, which has an increased capacity for fermenting polysaccharides relative to the lean-associated microbiome, is another way to achieve this objective, and addresses the significant obesity issues especially prevalent in Western societies.

In yet another embodiment, bioadhesive strips are provided that have encapsulated structures that are filled with desired agents, including but not limited to tomatidine and/or microbes, especially bacteria that are found in an individual's oral microbiome, such that effective amounts of the agents can be administered to treat particular diseases including muscle atrophy. Preferably, the bacteria comprise bacteria that are found in the communities of healthy mouths, including, for example, *Streptococcus, Actinomyces, Veillonella, Fusobacterium, Porphromonas, Prevotella, Treponema, Neisseria, Haemophilus, Eubacteria, Lactobacterium, Capnocytophaga, Eikenella, Leptotrichia, Peptostreptococcus, Staphylococcus*, and *Propionibacterium*. Such strips may be manufactured to have desired dissolvable aspects thereto and that further have encapsulated portions that house desired agents, such as but not limited to tomatidine, p53 protein, statins, PTEN, rapamycin, and other agents able to treat cancer symptoms.

Some bacterial pathogens actively inhibit p53 protein and induce its degradation, resulting in alteration of cellular stress responses. For example, in gastric epithelial cells infected with *Helicobacter pylori*, a bacterial pathogen that commonly infects the human stomach, gastric cancer is more common. In addition to H. pylori, a number of other bacterial species also inhibit p53, providing further evidence that host-bacteria interactions reveal that bacterial infections are associated with tumorigenesis. Inhibition of p53 may provide certain benefits to bacteria, for example, because it is believed that the inhibition of p53 may allow bacteria to subvert the host cell cycle control and apoptosis mechanisms, resulting in inhibition of cell death and survival of host cells damaged by infection.

In certain embodiments, CRISPR-Cas systems are employed to interfere with the p53 degradation abilities of particular bacteria that are known to degrade or otherwise interfere with the ability of p53 to function. As such in certain embodiments, the bacterial species is selected from the group consisting of a *Chlamydia* species, *Shigella flexneri, Mycoplasma* bacteria, and *H. pylori*.

The methods described herein are useful for treating and/or preventing (i.e., reducing the likelihood or risk of occurrence) different diseases, disorders, and conditions such as cancers and infectious diseases. Cancer remains the second most frequent cause of death in industrialized societies. Conventional therapies like surgery, radiotherapy, or chemotherapy remain the backbone of cancer therapy to date. Since the late 1980s, oncologists were successfully using the vaccine variant of *Mycobacterium bovis* BCG (Bacille Calmette-Guerin) as agent to prevent relapses of bladder cancer after surgical removal of the primary tumor. Although the exact mode of action of the bacteria is not fully understood, they might enhance the immune response against the cancer cells by, for example, activation of natural killer cells. Modification of BCG to express particular agents, such as tomatidine, p53, statins, rapamycin, etc. forms aspects of various embodiments of the present invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material. Incorporated herein by this reference are the following US patent publications: US Patent Publication Nos. 20140030332 to Baron, et al., and 20070123448 to Kaplan et al.; 20160000841 to Yamamoto, et al.; 20160095316 to Goodman et al.; 20160158294 to Von Maltzahn; 20140294915 to Kovarik; U.S. Pat. No. 8,034,601 to Boileau et al.; 20130225440 to Freidman, et al., 20150071957 to Kelly et al., 20160151428 to Bryann et al.; 20160199424 to Berry et al.; 20160069921 to Holmes, et al.; 20160000754 to Stamets; and U.S. Pat. No. 9,044,420 to Dubensky, Jr, et al. U.S. Pat. No. 8,357,368 to Dudek et. al.; U.S. Pat. No. 9,295,682 to Nunes; 20160354416 to Gajewski; 20120276143 to O'Mahoney, et. al.; 20160271106 to Shi, et. al.; U.S. Pat. No. 8,362,206 to Wallach; 20160354416 to Gajewski, et. al., 20170020932 to Cutcliffe, et. al.; 20170042924 to Otsuka et. al.; 20160243132 to Adams, et. al.; 20160175327 to Adams, et. al.; 20160271106 to Shi, et. al.; U.S. Pat. No. 8,362,206 to Wallach; 20160354416 to Gajewski, et. al., 20170020932 to Cutcliffe, et. al; U.S. Pat. No. 8,357,368 to Dudek et. al.; U.S. Pat. No. 9,295,682 to Nunes; 20160354416 to Gajewski; 20120276143 to O'Mahoney, et. al.; U.S. Pat. Nos. 8,829,165; 8,859,741; 9,045,547; 8,030,457 and 20140364460 to Reddig.

While the provision of microbes, preferably bacteria, to a person suffering from cancer is via their gut microbiome, other microbiomes may be employed, e.g. other than the microbes that colonize the gastrointestinal (GI) tract, as there exist microbiomes on the skin, and in other epithelial and tissue niches such as the oral cavity, nasal passages, eye surface and vagina. Each of these microbiomes may be targeted for delivery of therapeutic agents to address cancer issues, including muscle atrophy associated with cancer. The gastrointestinal tract (as well as the other mentioned microbiomes) harbors an abundant and diverse microbial community, including diverse strains of bacteria. Hundreds of different species may form a commensal community in the GI tract in a healthy person, and this complement of organisms evolves from the time of birth to ultimately form a functionally mature microbial population. A healthy microbiota provides the host with multiple benefits, including colonization resistance to a broad spectrum of pathogens, essential nutrient biosynthesis and absorption, and immune stimulation that maintains a healthy gut epithelium and an appropriately controlled systemic immunity.

In one embodiment of the present invention, a method and system and composition is provided to populate a person's microbiome, preferably their oral or gut microbiome, to restore, maintain or promote health of the individual and/or to alter a dysbiosis. For example, periodontal disease, a common chronic inflammatory disorder, has been associated with increased risk of postmenopausal breast cancer, particularly among former smokers who quit in the past 20 years. There is a need to design microbial compositions so that they possess a plurality of beneficial properties that would enhance the utility and commercialization of a microbial composition, especially those modified to produce desired agents, such as tomatidine. The human gut microbiota contains more than 500-1000 different phylotypes belonging essentially to two major bacterial divisions, the *Bacteroidetes* and the *Firmicutes*. The enhanced metabolic activities of the colonized gut ensure that otherwise indigestible dietary components are degraded with release of byproducts providing an important nutrient source for the host. Similarly, the immunological importance of the gut microbiota is well-recognized and is exemplified in germ-free animals which have an impaired immune system that is functionally reconstituted following the introduction of commensal bacteria. T cell development and differentiation may require colonization by specific commensal microorganisms.

In yet further aspects of the present invention, the treatment of cancer and cancer cachexia can be addressed by administering to an individual a desired amount of a bacteria modified (preferably via CRISPR-Cas systems) to produce predetermined levels of tomatidine and/or p53 protein, or other agents, e.g. rapamycin, statins, an immune checkpoint inhibitor, etc. Inclusion of DNA in microbes to produce, for example, certain amounts of wild-type p53 protein in a person's microbiome is one way in which to administer amounts to a person's body in a manner that can be tolerized to such amounts. Effective ways to ensure that the type, amount, and timing of desired administration is achieved is made possible by the ability to promptly address the survival of these modified microbiomes by use of antibiotics, or any number of other ways to either increase or decrease the efficiency of such modified microbes. Such a system and method addresses concerns with respect to proper timing of amounts that the person is being properly exposed to due to effective ways to control the administration of such factors, proteins, drugs, etc. via one's microbiome. The particular protein degradation pathway which seems to be responsible for much of the muscle loss seen in a muscle undergoing atrophy is the ATP-dependent, ubiquitin/proteasome pathway. In this system, particular proteins are targeted for destruction by the ligation of at least four copies of a small peptide called ubiquitin onto a substrate protein. In skeletal muscle, the E3 ubiquitin ligases atrogin-1 and MuRF1 are known to play essential roles in protein degradation and muscle atrophy. Provision of modified microbes to an individual's microbiome is one way in which to alter the course of such muscle wasting, as further described herein.

The bone is a common site of metastasis for several malignancies. The impact of metastasized tumor cells in the bone disrupts the balance between the activities of the osteoclasts and osteoblasts. Radiographically, bone lesions are classified as being osteolytic (bone loss) or osteosclerotic (bone formation) or mixed. It is known that Osteopontin is expressed by tumor cells and stimulates osteoblast differentiation. Osteopontin is a pro-inflammatory cytokine and is implicated in the progression of liver tumors, as well as other tumors. Tumor cells with a competent Hedgehog pathway are more potent at inducing osteoblast differentiation. The Hedgehog pathway plays an essential function in regulating cell fate and in developmental patterning in humans and is important in the formation of the skeleton. During skeletogenesis and endochondral ossification, Hedgehog pathway signaling coordinates growth and differentiation. Reactivation of the Hedgehog pathway has been implicated in a wide variety of cancers and carcinogenesis. Various embodiments of the present invention are directed to providing modified microbes to an individual's microbiome such that the Hedgehog pathway is affected in a manner to restore health to an individual, e.g. via expression of various factors by such modified microbes in the individual's microbiome.

Tumor cells initially enhance the differentiation of osteoblasts that in turn, express osteoclastogenesis enhancing factors. Later, as the osteoblasts get eliminated, an environment is created that stimulates osteoclast differentiation and activity. Thus, an active Hedgehog pathway signaling in tumor cells facilitates the generation of an osteoclast-stimulating milieu by initially kick-starting osteoblast development. Tumor cells can alter the balance between the activities of osteoblasts and osteoclasts via Hedgehog pathway signaling. For example, breast cancer cells express Hedgehog pathway ligands and the Hedgehog pathway signaling propels breast cancer progression. Administration of pharmacological Hedgehog pathway inhibitors can inhibit Hedgehog pathway signaling in breast cancer cells. Hedgehog pathway proteins and genes have also been implicated in esophageal cancer, stomach cancer, prostate cancer, ovarian cancer, biliary tract cancer, glial cell cancer, multiple myeloma, colon cancer and melanoma. While not bound by theory, tomatidine is believed to interfere with the Hedgehog pathway and may inhibit the actions of the pro-inflammatory cytokine Osteopontin.

Hedgehog pathway signaling in tumor cells is essential to the development of osteolytic metastases. Soluble factors, that include Osteopontin (OPN) and other Hedgehog pathway ligands, are secreted by tumor cells, and are thought to enhance osteoblast differentiation and mineralization activity. Tumor cells initiate osteoblast differentiation and the expression of osteoclastogenic factors is seen as an early event, followed by elimination of osteoblasts later. Thus, the overall microenvironment in cancer progression appears to shift in favor of osteoclastogenesis. An active Hedgehog pathway signaling and expression of OPN are important attributes for a tumor cell to activate osteoclast differentiation and resorptive activity.

Blocking the Hedgehog pathway interferes with the transcription of Osteopontin (OPN). Cyclopamine treatment decreases the activity of the OPN promoter in a dose-dependent manner. In contrast, tomatidine, the structural analog of cyclopamine, has apparently no effect on the promoter activity of cyclopamine. This is surprising but reveals that the particular mode of action of tomatidine in the body is as yet not fully known.

Tumors are now recognized as comprising a mosaic of genetically different and actively mutating cells rather than a single type. Thus, combination drug therapies are being advocated to combat tumor cellular heterogenecity. Employing various methods of the present invention, it is believed that such combination therapies can be achieved by using an individual's own microbiomes, such that one or more drugs, factors, proteins, (e.g. tomatidine, statins, and p53) can be provided to an individual through the modification of the individual's microbiome.

In spite of great advances in understanding pathways related to cancer and cancer therapy, there is a need to provide new anticancer treatments that do not cause toxicity to healthy cells and that are effective in treating cancer, and especially the cachexia associated therewith. The present invention provides such a treatment option, and one that is in many ways, more subject to the inherent control aspects of the human body as it relies upon the long established but poorly understood relationship between diseases and the microbiomes of humans.

In still other embodiments of the present invention, embodiments relate to the employment of anti-muscle atrophy characteristics of tomatidine as described herein, but further involve the employment and production of anticancer proteins via the microbiome of an individual, e.g. that are capable of oral administration, and are preferably stable at room temperature, and in some embodiments also have potent antiviral activities that can be useful in a significant percentage of human cancers that are caused by viral infections. One aspect of the present invention is directed to the use of CRISPR-Cas systems to provide a better p53 protein that is much more stable so that its folding is preserved, thus protecting its tumor suppressing function. In particular, the regions where the protein are most vulnerable to mutations that cause improper folding are targeted and revised so as to impede such mis-folding events.

The microbiota inhabiting our bodies influence cancer predisposition and etiology. The largest microbial community in the human body resides in the gut and comprises somewhere between 300 and 1000 different microbial species. The human oral microbiome and the bacteria inhabiting such microbiome are, in certain circumstances, also effective as agents in the treatment of cancer. Various embodiments of the present invention involve the modification of at least two, if not three separate microbiomes of a person to treat certain conditions. For example, the treatment for cachexia may be achieved via modification of an individual's oral microbiome via the delivery of particular bacteria designed to produce therapeutic amounts of tomatidine. The simultaneous provision of bacteria to the individual's gut microbiome that are designed to produce therapeutic amounts of p53 protein can also be achieved, with the two separate microbiomes being employed to address separate but related issues involved in cancer treatments. This particular aspect of the present invention, while simple in nature, is believed to have profound effects in avoiding undesired drug interactions that can complicate treatment regimens. By having different microbiomes of the same individual administer different desired compounds, drugs, factors, proteins, etc. to the person's body, the ability to separately control administration and amounts (as well as to address issues by killing bacteria in one but not the other microbiome) is rendered feasible as a way to administer desired cancer fighting agents to an individual.

Still other aspects of the present invention are directed to the use of antibodies against certain oral bacteria, e.g. *P. gingivalis*—which is a pathogen known to contribute to periodontal disease and that has been associated with the risk of pancreatic cancer, and lung cancer, colorectal cancer and cancers of the stomach, oesophagus, and cancers of the head and neck. Microbes mediate the relationships with these types of cancer and epidemiologic evidence exists that shows the association between the human microbiome and these types of cancer. Particular embodiments relate to an association of the oral microbiome and periodontitis with pancreatic cancer, with a strong positive association being noted between periodontitis at baseline and subsequent risk of fatal pancreatic cancer. Men with periodontal disease have a 64% higher risk of pancreatic cancer compared to those reporting no periodontal disease and have a 4-fold increase in risk of pancreatic cancer. Elevated antibodies to *P. gingivalis* have been associated with a 3-fold increase risk of aerodigestive cancer mortality.

One aspect of the present invention is directed to the use of commensal and symbiotic microbiota that have tumor-suppressive properties. It is believed by the present inventors that the associations between diet and cancer risk is explained by differences in microbiota among the participants and that the employment of probiotics and prebiotics is an effective chemoprevention strategy that can be utilized to promote health and cancer treatment and recovery. Enhancing the microbiota of an individual with particular microbes, such as those modified by CRISPR-Cas systems, to include, for example, the provision of one of p53 protein expression or tomatidine expression, and preferably with the co-administration of statins to combat the oncogenic nature of mutant p53, is one of the aspects of various embodiments of the present invention.

While cancer has been largely perceived as an intrinsic problem of body homeostasis, and infection a problem of external environment, the present inventors believe that the effective treatment of both diseases converges in that premalignant cell behavior is a mirror of cellular dysbyosis. Infection, like cancer, is a lack of regulation of important cells of the superorganism of the human body in concert with its integral microbiomes. There appears to be a strong association between the human microenvironment, sustained inflammation, and cancer. Growing evidence has emerged that, for example, the oral microbiome and periodontitis has a profound impact with respect to the pathogenesis and risk of various malignancies.

One aspect of the present invention relates to a paradigm shift from the classic germ theory so prevalent in western medicine during the last century. Viewing the microbiome of a person as an integral part of the human person in terms of health, much as an organ of such individual, is a more correct and useful concept as it relates to understanding cancer (as well as other diseases) and in treating the same. Just as methods for addressing microbe based diseases has advanced recently, the ability to address cancer treatments from a new perspective is critical in advancing effective treatments to avoid if not cure various cancers. There are parallels between infection by microbes and cancer from various perspectives. For example, a single infection can arise from a single microbe, just like a cancer can be initiated by a single cell, and then spread to establish tumors and metastatic disease. In both cases, disruption of homeostasis allows for pathological bacterial expansion and may lead to full blown infection. But not all pathologic microbes lead inevitably to infection, as such a course is arrested by immune system responses. Similarly, precancerous cells and tissues do not always progress to full blown cancer, but rather, the progression of cancer is hindered or halted by the immune system. Premalignant cell behavior is a virtual mirror to microbial dysbiosis. Cancer, like infection, can be viewed as a dysbiosis of a person's microbiome. Various embodiments of the present invention are directed to correcting dysbiosis and in maintaining a healthy balance of microbes so as to promote human health, e.g. via administration of microbes modified by CRISPR systems to express agents to address various disease states.

Despite the success of colonoscopy screening, colorectal cancer remains one of the most common and deadly cancers, and colorectal cancer incidence is rising in some countries where screening is not routine and populations have recently switched from traditional diets to western diets. Colorectal cancer represents an important disease as one of the major causes of death worldwide. As disclosed herein, various methods are presented to combat colorectal cancer, including the provision of modified BCG bacteria able to express competently folded p53.

More than 50,000 people are diagnosed with pancreatic cancer every year, and because the disease is often not diagnosed until an advanced stage, less than 10% of those diagnosed will still be alive in five years. People with two types of periodontal disease have a greater risk of subsequently developing pancreatic cancer, showing that markers of pancreatic cancer can be found in oral microbiome dysbyosis. Oral bacteria is the underlying explanation due to periodontitis being caused by oral bacteria dysbiosis. For example, individuals who have *Porphyromonas gingivalis* in their oral microbiome have an almost 60% greater risk of developing pancreatic cancer relative to those who do not have such bacteria in their oral microbiome. Similarly, individuals with *Aggregatibacter actinomycetemcomitans* present in their oral microbiome have at least a 50% increased relative risk of developing pancreatic cancer. Thus one aspect of the present invention is directed to the establishment of and maintenance of an oral microbiome of an individual such that there are less robust populations of at least one of *Porphyromonas gingivalis* and *Aggregatibacter actinomycetemcomitans* in a person's oral microbiome. One way this is accomplished is the employment of oral strips impregnated with beneficial bacteria so that a preferred population of bacteria can be established in a person's oral cavity, preferably after an antibiotic treatment to destroy undesired bacteria.

One of the major challenges to detecting pancreatic cancer is its late clinical presentation. By the time pancreatic cancer is diagnosed, the cancer is usually well-advanced. Pancreatic adenocarcinoma is a low-incident but highly mortal disease. It accounts for only 3% of estimated new cancer cases each year but is currently the fourth common cause of cancer mortality. By 2030, it is expected to be the 2' leading cause of cancer death.

In one aspect of the present invention, a method includes the bacterial analysis of an individual's stool in a non-invasive way for screening for pancreatic cancer. Preferably, a non-invasive, stool-based screening tool for colorectal cancer is employed and a kit is used such that patients can use and send the kit in via mail for evaluation. Once diagnosed, the employment of modified microbes to the individual's microbiome is achieved to combat the progression of such cancer, e.g. by the co-administration of statins to interfere with the oncogenic properties of mutant p53, while the microbes provide wild-type p53 to control further cancer growth, and with still other microbes providing amounts of tomatidine to thwart muscle atrophy.

Throughout evolution, bacteria progressively acquired virulence factors and the disease-promoting and pro-carcinogenic effects of pathogens depend on these virulence factors, often comprising adhesion molecules, which confer the ability to adhere to and invade the tissues of the human body. One aspect of the present invention is directed to the modification of such adhesion molecules so that pathogenic bacteria are altered in a manner that reduces their abilities to adhere to tissues of the human body, thus lessening various human diseases.

Chronic and/or excessive consumption of alcohol has been found to be an important risk factor for many cancers, including colorectal cancer. Microbial metabolism may contribute to the toxicity of alcohol, especially in the gastrointestinal tract, where aerobic and facultative anaerobic bacteria convert ethanol to acetaldehyde. Indeed, acetaldehyde is known to be a highly toxic and pro-carcinogenic compound with various negative effects, ranging from DNA damage and impaired DNA excision repair to the degradation of folate. Thus one aspect of various embodiments of the present invention is directed to providing particular bacteria to a person who consumes alcohol in a manner that lessens the risk of cancer via the ability of such bacteria to ameliorate the accumulation of acetaldehyde. The conversion of ethanol to acetaldehyde is inhibited by the use of antibiotics, such as ciprofloxacin, which kills primarily aerobic and facultative anaerobic bacterial populations. Thus, to reduce the undesired effects of alcohol conversion to acetaldehyde, the use of specific antibiotics, followed by the use of probiotics and/or fecal transplantation protocols, is one aspect of the present invention that may be employed to combat colorectal cancer-associated dysbiosis and thus restore eubiosis in chronic diseases, helping to reduce microbiota-induced genotoxicity and activation of inflammatory, proliferative and pro-carcinogenic pathways. The gut microbiota plays a major role in the promotion and progression of colorectal cancer via several mechanisms, including inflammation, metabolism and genotoxicity, and thus, targeting an individual's microbiota is an effective way to treat, if not prevent, colorectal cancer. Particular bacterial species have been identified that are suspected to play a role in colorectal carcinogenesis, including *Streptococcus bovis, Helicobacter pylori, Bacteroides, fragilis, Enterococcus faecalis, Clostridium septicum, Fusobacterium* spp. and *Escherichia coli*. Certain embodiments of the present invention are directed to the modification of such microbes to either hinder the effects of virulence factors and/or to enable such microbes to express desired amounts of non-mutant p53, statins (to address mutant p53 functioning), and/or tomatidine to enhance muscle maintenance, etc.

Cancer incidence is low in the Ohio Amish and it is believed by the present inventors that the presence of *Prevotella* bacteria as one of the more predominant bacteria in both their oral and gut microbiomes, is related to such lower cancer incidence. The gut microbiota of various livestock species has been reported to contain a high relative abundance of the xylanolytic bacterial species *Prevotella*. The present inventors submit that the environment plays an important role in modulating bacterial community composition and that transmission of gut microbes occurs across host species. Gut microbial communities often contain many *Bacteroides* or their close relatives, *Prevotella*. One aspect of certain embodiments of the present invention is directed to increasing the prevalence of *Prevotella* populations in individuals so as to lessen the chances of cancer developing in such individuals. Still other embodiments are directed to the modification of *Prevotella* bacteria in a manner that makes them less virulent, but that still maintains the beneficial effects of such bacteria in various microbiomes, such as the oral and gut microbiomes, e.g. by reducing the expression of virulence factors of *Prevotella*.

Another aspect of the present invention is directed to expression of particular tumor suppression agents by microbes, e.g. such as *Prevotella*, in an individual's microbiome. Among tumor suppressor agents, the p53 protein is a transcription factor that recognizes and binds to specific DNA response elements and activates gene transcription. P53 is a tumor suppressor that has a role in the maintenance of genomic integrity and as a guardian of DNA. p53 secretion and uptake by cells demonstrates that p53 is a transmissible particle. Stress triggered by ionizing radiation or other mutagenic events leads to p53 phosphorylation and cell-cycle arrest, senescence, or programmed cell death. Tumor suppressors are complex macromolecules normally occurring as multi-domain proteins flanked by disordered segments. The tumor-suppressor p53 is a transcriptional factor that exerts broad anti-proliferative effects, including growth arrest, apoptosis, and cell senescence after cellular stress, and has been described as the most frequently mutated gene in a cancer cell. The end regions of tumor suppressor p53 act as molecular antennas for proper activity and interactome signaling. Although classified as a transcription factor, p53 can also mediate apoptosis.

Most human viruses impair p53 activity. For example, in cervical cancer, the human papillomavirus E6 protein targets p53 for degradation. Bacterial infection is known to trigger the p53 pathway and activates p53 isoforms. Another aspect of the present invention is directed to the involvement of p53 aggregates in cancer pathogenesis and progression. The production of competent p53 by bacteria in a person's microbiome is a better way in which to provide sufficient amounts of p53 to suppress tumorgenesis. Thus, one aspect of the present invention relates to the use of CRISPR-Cas to modify bacteria to express p53 proteins, and preferably a more stable p53 protein in that its folding is preserved, thus protecting its tumor suppressing function. In such embodiments, the regions where the protein are most vulnerable to mutations that cause improper folding are targeted and revised so as to impede common mis-folding events.

In yet other embodiments, cancer cells are infected with modified bacteria having thermosensors, thus making such cancer cells amenable to some controls incorporated therein, such as by adjusting the temperature to turn on certain genes—with such genes encoding toxins. Alternatively, one is able to shut off the genes by adjusting the temperature, thus selectively killing or modifying the behavior of the cells infected by the bacteria.

The prokaryotic type II CRISPR-Cas9 (clustered regularly interspaced short palindromic repeats—CRISPR-associated 9) system is rapidly revolutionizing the field of genetic engineering, allowing researchers to alter the genomes of a large range of organisms with relative ease. Experimental approaches based on this versatile technology have the potential to transform the field of cancer genetics. As discussed herein, CRISPR systems (including not just Cas9, CasX, Casy, etc.—but also other similar and as yet to be designed CRISPR systems) can be employed in various ways to modify microbes such that they can be administered to individuals so as to enhance human health by interfering with disease progression, and especially cancer progression.

Yet another aspect of the present invention relates to an increased risk of pancreatic cancer in patients with *Helicobacter pylori* (*H. pylori*), which is believed to be also dependent on particular blood types. An association between pancreatic cancer risk and CagA-negative *H. pylori* seropositivity is found among individuals with non-O blood type, but not among those with an O blood type. The differences in terminal binding antigens in gastrointestinal mucins for individuals with non-O blood type (A and B), influences the binding potential of the *H. pylori*. Thus, certain embodiments are directed to addressing pancreatic cancer by the modification of *H. pylori* to interfere with its normal binding potential, such that elimination of resident *H. pylori* in a person's stomach, followed by administration of the modified microbes, can establish a population of bacteria that is better for the person's health and that is less prone to result in the progression of pancreatic cancer.

There is also a perceived link between oral disease and pancreatic cancer and the bacteria found in certain types of gum disease is linked to a 2× greater risk of developing pancreatic cancer. Pancreatic cancer, which is difficult to detect and kills most patients within six months of diagnosis, is responsible for 40,000 deaths a year in the United States. Antibodies for oral bacteria are indicators of pancreatic cancer risk. In certain embodiments of the present invention, the oral microbiome of individuals who have or are at risk of having pancreatic cancer are administered beneficial bacteria to their oral cavities, preferably via the oral strips as described herein, impregnated with modified microbes that may out-compete the native bacterial populations and also administer desired amounts of beneficial agents, e.g. tomatidine, p53, statins, in a manner that effectively treats the pancreatic cancer.

MicroRNAs (miRNAs) are short, noncoding RNAs that regulate target mRNAs via transcript degradation or translational repression. Cell- and tissue-specific miRNA expression profiles are altered in numerous disease states. Inflammatory bowel diseases (IBD) are a major risk factor for the development of colon cancer. The loss of all of the intestinal miRNA results in impaired barrier function and inflammation similar to IBD. Circulating miRNA profiles are known to correlate with miRNA expression changes in diseased tissue. While conventional efforts to treat cancer have focused on the inhibition/destruction of tumor cells, strategies to modulate the host microbiota and miRNAs-induced inflammation offer a new way by which to combat what has been a terribly difficult disease to address. Antibiotic treatment causes disturbance of the microbiota, and probiotics, prebiotics and fecal microbiome transplantation may be employed to restore the dysbiosis caused thereby. An individual's microbiota is tied into certain cancers, including colorectal cancer, by induction of a chronic inflammatory state, leading to the production of toxic metabolites. Microorganisms frequently found in IBD patients include different species that are well known butyrate producing bacteria, which are linked to disease severity. Butyrate is a short chain fatty acid which is a byproduct from fermentation of non-digestible carbohydrates such as resistant starch, pectin, cellulose, and unabsorbed sugars. Short Chain Fatty Acids (SCFAs) play an essential role in the health of the colonic epithelial cells and intestinal barrier function. Butyrate decreases colonic epithelial permeability. Butyrate is an energy source for enterocytes, the cells that line the intestinal wall. Butyrate mediates the colonic inflammatory response and is thought to be a preventative against colon cancer. Butyrate can prevent the overgrowth of pathogens and promotes immune system T regulatory cells.

Certain embodiments of the present invention are directed to the purposeful modification of an individual's microbiome that entails initial reduction in the amount of butyrate to permit healing of certain tissues, followed by the reintroduction of butyrate, but with the inclusion of modified microbes as described herein that are designed to competivley compete with native strains and that further provide beneficial agents to establish and maintain a healthier microbiome so as to thwart the progression of diseases. Thus, one aspect of the present invention relates to the modification of an individual's microbiota to reduce the amount of butyrate producing bacteria, or at least the amount of butyrate by the bacteria present in an individual's microbiota, especially their gut microbiome, for a period of time, within which tissues can heal and resident bacterial populations can be altered.

Molecular mechanisms modulated by gut microbiota promote inflammation and support colorectal carcinogenesis. Both endogenous and exogenous miRNAs modulate tumor-related inflammation in colorectal cancer. Gut microbiota has an influence on colorectal carcinogenesis and the microbe population living in the human intestine plays a significant role in the development and progression of colorectal cancer. Maintenance of a healthy intestinal epithelia is critical to provide optimal nutrient absorption, as well as an efficient immune barrier. The balance between intestinal microbiota, intestinal epithelium and host immune system is decisive for normal functionality of the intestinal cells. Therefore, changes in any of these three factors may influence the functionality of the intestinal epithelium. The benefits of the body in relation to gut microbiota are related to extraction of the energy from the fermentation of undigested carbohydrates and from the absorption of short-chain fatty acids. Butyrate is the most important of these fatty acids being metabolized by the colonic epithelium and is the favorite energy source of colonocytes. The most important bacteria producing this fatty acid are *Faecalibacterium prausnitzii*, which belongs to the *Clostridium leptum* cluster, and *Eubacterium rectale/Roseburia* spp., which belong to the *Clostridium coccoides*. In healthy colonocytes, butyrate hampers apoptosis and further mucosal atrophy. In colorectal cancer cells, butyrate has been proved to stimulate differentiation and impede cell proliferation. Butyrate protects human colon cells from DNA damage. In addition to butyrate, gut microbiota are also implicated in the constitution of another category of beneficial fatty acids, such as conjugated linoleic acids, having anti-inflammatory and cancer protective properties. Increasing the production of such useful agents by bacteria or microbes that form part of a person's microbiome is yet another aspect of various embodiments of the present invention, and the employment of CRISP-Cas systems to achieve such modifications is a preferred method.

The composition of gut microbiota evolves throughout human life, from birth to old age, and is modulated, temporarily or permanently, by many factors such as dietary components, environment, age, stress, treatment (medical or surgical) and disease. Antibiotic-based therapy represents one of the most important factors with the effect on the composition of the microbiota. This therapy can cause diarrhea which generally is associated with altered intestinal microbiota resulting in enteropathogens overgrowth, loss of mucosal integrity and altered metabolism of vitamins and minerals.

Individuals can be classified into one of three prevalent variants or "enterotypes" according to the abundance of predominant genera which are *Bacteroides, Prevotella* and *Ruminococcus*. *Bacteroides* enterotypes are related to amino acids, animal proteins and saturated fats, constituents typical to Western diet, while *Prevotella* is connected to carbohydrates and simple sugars, suggesting an interconnection with a carbohydrate-based diet more common of rural societies.

Individuals whose microbiota are mainly *Bacteroides* and commute their dietary patterns to a diet based on high proportions of carbohydrates, will acquire a *Prevotella* enterotype in the long term. Substantial changes in the composition of fecal microbiota are detectable in a few days after carbohydrate intake, demonstrating that diet rapidly and reproducibly alters the human gut microbiome. Numerous studies indicate that fruit, vegetable and a high-fiber intake, particularly of cereals and whole grains, is associated with a decreased risk of colorectal cancer, while diets that are rich in red and processed meat, fat and alcohol are associated with an increased risk of the disease. Higher dietary intakes of animal products may modify gut microbiota and consequently play an important role in carcinogenesis.

One aspect of the present invention is the modification of an individual's gut microbiome such that they harbor far less of the bacteria *Streptococcus bovis, S. bovis* bacteremia, *Clostridia, Bacteriodes* and *Helicobacter pylori*, all of which have been involved in the pathogenesis of cancer.

Conversely, bacteria like *Lactobacillus* and *Bifidobacterium* have anticarcinogenic effects, which are believed to involve inactivation of microbial enzymes that are important for pro-carcinogen activation. *L. casei* and *L. acidophilus* decrease the activity of β-glucuronidase, azoreductase, and reflect that the balance of activation and detoxification supports the belief that the microbial community structure plays a significant role in the initiating step of carcinogenesis. One aspect of the present invention relates to the favorable modulation of the gut microbiota structure to reduce the risk of cancer development e.g. by the clinical use of probiotic in the prevention of cancer. In various embodiments, the probiotic supplementation of an individual's microbiome is able to modify microbiota structure by reducing enterobacteria like *Salmonella/Shigella* and increasing lactic acid bacteria and *Bifidobacteria* to provide a protective role of such probiotics. Other embodiments are directed to purposefully modifying an individual's microbiome to enable the person to have a *Prevotella* enterotype in place of the bacterial enterotype they previously possessed. This is again preferably achieved via the provision of desired bacteria, prebiotics and probiotics in a fashion such that the gut microbiome of the individual is adapted to host *Prevotella* bacteria as a substantially stable bacteria culture within the person's microbiome.

Inflammatory bowel diseases (IBD) are induced and preserved by diverse microorganisms and frequently involves signs of global dysbiosis, according to changes in the number, diversity and stability of microbiota. Increasing evidence shows that dysbiosis induces the production of genotoxins and metabolites associated with tumorigenesis and produces disorder of the immune response which promotes and maintains inflammation in IBD leading to colorectal cancer. Microorganisms frequently found in IBD patients include different species of *E. coli*, species of *Chlamydia, Mycobacterium, Clostridia, Candida*, as well as *Proteus mirabilis, Klebsiella pneumonia* and diverse *Proteobateria*, including *Helicobacter. Firmicutes* and *Bacteroidetes* decrease in IBD. Different bacterial species contribute to the pathogenesis of IBD, with enhanced activation of transcription factor NF-κB, an important regulator of inflammatory processes. NF-κB suppression improves IBD development, and NF-κB dependent cytokines are key agents which signal from inflammatory cells to tumor cells. In chronic inflammation, proinflammatory cytokines, such as TNF-α, can induce DNA damage through reactive oxygen species (ROS) and nitrogen species, which leads to tumor initiation. TGF-β is a powerful pleiotropic cytokine with immune suppressing and anti-inflammatory properties, inhibiting cell cycle progression and promoting apoptosis. Inflammatory bowel diseases (IBD) are a major risk factor for the development of colon cancer, by a mechanism called in literature colitis-associated cancer (CAC). The increased prevalence of CAC in IBD patients is influenced by disease severity and duration, and by the efficacy of anti-inflammatory therapies It seems that IBD are induced and preserved by various microorganisms and frequently involves signs of global dysbiosis, according to changes in the number, diversity and stability of microbiota. Increasing evidence shows that dysbiosis induces the production of genotoxins and metabolites associated with tumorigenesis and produces disorder of the immune response which promotes and maintains inflammation in IBD leading to cancer. Thus, in various embodiments, the modification of an individual's microbiome to address specific dysbyosis is achieved by the purposeful administration of microbes to an individual's microbiome that express desired agents, such agents preferably included in the modified bacteria via CRISPR systems, with attendant expression controls provided to safely maintain desired populations of bacteria in the microbiome so as to promote long term health.

Reactive oxygen species (ROS), a group of highly reactive ions and molecules, are increasingly being appreciated as powerful signaling molecules involved in the regulation of a variety of biological processes. Extensive research over the past half a century indicates that reactive oxygen species play an important role in cancer as cancer cells have increased ROS levels in comparison to their normal counterparts. This is believed to be partly due to an enhanced metabolism and mitochondrial dysfunction in cancer cells. The escalated ROS generation in cancer cells contributes to the biochemical and molecular changes necessary for tumor initiation, promotion and progression, and often, tumor resistance to chemotherapy. Therefore, increased ROS in cancer cells presents an ability to eliminate cancer cells by elevating ROS to highly toxic levels intracellularly, thereby activating various ROS-induced cell death pathways, or inhibiting cancer cell resistance to chemotherapy. So while high levels of ROS may be useful in treating certain cancers, low levels of ROS can also be beneficial, as it has been shown that excessive accumulation of ROS can also promote certain types of cancer. Thus, particular aspects and embodiments of the present invention are directed to adjusting the levels of ROS production by cells in the microbiome of individuals so as to deter the growth of cancer. Certain embodiments involve the recognition that a characteristic of cancer cells that distinguishes them from normal cells is their ability to produce increased numbers of ROS and their increased dependence on an antioxidant defense system. ROS are produced as a byproduct intracellularly by mitochondria and other cellular elements and exogenously by pollutants, tobacco, smoke, drugs, xenobiotics, and radiation. ROS modulate various cell signaling pathways, which are primarily mediated through the transcription factors NF-κB and STAT3, hypoxia-inducible factor-1α, kinases, growth factors, cytokines and other proteins, and enzymes. These pathways have been linked to cellular transformation, inflammation, tumor survival, proliferation, invasion, angiogenesis, and metastasis of cancer. Regulation and control of the amount of ROS to which cancer cells are exposed, preferably via interactions with an individual's microbiome that has been modified via the introduction of microbes, and specifically bacteria, that have been rendered capable of producing ROS via being adapted using CRISPR-Cas systems, forms the basis of various embodiments of the present invention as described herein.

Potassium diazoacetate, a stable form of nitrosated glycine, has been found to initiate mutations in the p53 gene, supporting the hypotheses that NOC linked to glycine subscribes to p53 mutations in humans. High levels of polyamines are toxic and are associated with several diseases, including cancer, and oxidative stress that results from polyamine catabolism is the underlying mechanism of toxicity. Several pathogens, including *Shigella flexneri, Streptococcus pneumoniae, Salmonella enterica* and *H. pylori*, utilize polyamines to increase their virulence. One aspect of the present invention is to reduce the virulence of various bacteria found in a person's microbiota by employing CRISPR-Cas systems (or similar systems) to modify, if not remove the virulence abilities of various microbes to produce virulence factors. Thus, modified microbes that produce little polyamines are employed in various embodiments of the present invention to restore health.

Chronic inflammation can deeply alter local immune responses and cause the liberation of nitric oxide. ROS can be produced by the gut microbiota or generated by immune cells during inflammation. Gastrointestinal bacteria generate nitric oxide from nitrate and nitrite. ROS are potent mutagens that lead to DNA breaks, point mutations, and protein-DNA crosslinking and influence chromosomal instability and the risk of cancer. Thus, still other embodiments of the present invention are directed to the provision of modified microbes that address chronic inflammatory states by interfering with the liberation of nitric oxide.

MicroRNA (miRNAs) are small (21-25 nucleotide) non-coding RNAs (ncRNAs) that regulate the translation and stability of their specific mRNA targets. The aberrant expression of microRNAs is related to the initiation and progression of various cancers, with MiRNAs acting as tumor suppressors or oncogenes. Inflammation determines changes in expression of miRNAs, primarily through the actions of proinflammatory cytokines. The role of miRNAs is believed to be in the initiation and progression of human cancer, as well as in involvement with immune responses, inflammation, cell proliferation and cell death, all of which are known to be regulated by NFκB. The overexpression of certain miRNAs is believed to lead to the repression of tumor suppressor genes that promote tumor survival and cell migration through NF-κB activation. While the gut microbiota interacts directly with the host through the production of metabolites, peptides and other molecules, how microbiota regulates miRNA expression and contributes to the maintenance of intestinal homeostasis and to IBD pathogenesis is still largely unknown. miRNAs play a role in colonic carcinogenesis and their reduction by butyrate is an important mechanism of its anti-cancer effects. Thus, in certain embodiments, modified microbes are administered to an individual in need thereof to halt the overexpression of certain miRNAs responsible for the repression of tumor suppressor genes, such as p53. In concert with the administration of statins to interfere with the oncogenic effects of mutant p53, and with the expression by microbes of wild type p53, it is believed that the progression of many types of cancer can be controlled.

p53 is altered in many tumors. Various treatment strategies have focused on targeting p53. About 50% of human tumors have TP53 gene mutations. Because formation of a tetrameric structure is critical for protein-protein interactions, DNA binding, and the post-translational modification of p53, a small destabilization of the tetrameric structure results in dysfunction of tumor suppressor activity. It is believed that the increase in total p53 seen in the progression of certain cancers reflects the fact that mutant p53 proteins are produced and that these mutant p53 proteins make cancer conditions worse, rather than better. Having wild type competently folded p53 generated by a perosn's microbiome can be employed to increase the number of "good" p53, while the use of other agents, e.g. those that modify mutant p53 to render it competent or at least neutral, but more preferably agents such as statins that ameliorate the "bad" effects of mutant p53, is one way to effectively treat cancerous conditions.

p53 tumor suppression protein is sometimes called "the guardian of the genome" as it is a key component of the cellular mechanisms controlling cellular responses to various cellular stresses. p53 is activated and primarily functions as a transcriptional regulator of expression of multiple effector proteins and miRNAs, which, in turn, regulate key cellular processes such as apoptosis, cellular proliferation, and autophagy. Since regulation of cellular stress responses is tightly intertwined with metabolic regulation, there is an interplay between p53 and multiple pathways involved in regulation of metabolism and cellular homeostasis that is complex and not fully understood. Approximately 50% of all human cancers have mutant p53, with approximately 75% of such cancers having a single amino acid residue missense mutation in the DNA-binding core domain. The p53 protein recognizes and binds to specific DNA response elements and activates gene transcription. The p53 gene is the most frequently mutated gene in cancer and is a transcriptional factor that exerts broad anti-proliferative effects, including growth arrest, apoptosis, and cell senescence. Stabilization of cancer progression is one objective of certain aspects of the present invention, with the co-administration of statins being employed to reduce the ill-effects of mutant p53 and with the expression of competently folded p53 by microbes administered to an individual believed to significantly affect the chances of survival, if not effective treatment, of cancer victims.

Despite the huge diversity in the genes implicated in tumorigenesis, the p53 transcription factor—encoded by the human gene TP53—stands out as a key tumor suppressor and a master regulator of various signaling pathways involved in this process. The many roles of p53 as a tumor suppressor include the ability to induce cell cycle arrest, DNA repair, senescence, and apoptosis. The p53 gene is mutated and gives rise to a stable mutant protein whose accumulation is regarded as a hallmark of cancer cells. Mutant p53 proteins not only lose their tumor suppressive activities but gain additional oncogenic functions that endow cells with growth and survival advantages. Aberrant forms of human p53 are associated with poor prognosis, more aggressive tumors, metastasis, and short survival rates in multiple tumor types.

Certain embodiments of the present invention are directed to a method that restores p53 via its expression by an individual's microbiome, such that tumors can be treated. Such methods involve a step of exposing cancer cells to bacteria that produce competently folded and thus effective, p53 proteins. Still other embodiments involve the co-production or administration of statins to an individual such that mutant p53 is prevented from enhancing the growth of cancer, thus permitting the positive anti-cancer effects of wild type, competently folded p53 to achieve positive, anti-cancer effects in a person suffering from cancer. p53 tumor suppressor has been identified as a protein interacting with the large T antigen produced by simian vacuolating virus 40 (SV40). Inhibition of p53 can be achieved by bacterial pathogens which actively inhibit p53 protein and induce its degradation, resulting in alteration of cellular stress responses. This phenomenon was initially characterized in gastric epithelial cells infected with *Helicobacter pylori*, a bacterial pathogen that commonly infects the human stomach and is strongly linked to gastric cancer. Besides *H. pylori*, a number of other bacterial species inhibit p53. Thus, certain embodiments of the present invention involve the neutralization of such p53 inhibiting agents, including antibiotic administration to deter the populations of various bacteria, such as *H. pylori*, preferrably coupled with the administration of microbes and bacteria that enhance the effects of p53 on fighting cancer, including the provision of statins that reduce the undesired effects of mutant p53, the expression of tomatidine to address cachexia, and rapamycin for anti-aging disease treatments, etc.

Various embodiments of the present invention are directed towards the direct interplay between bacterial pathogens and tumor suppression mechanisms that protect an individual from cancer development. Various pathogenic bacteria actively inhibit the major tumor suppression pathway mediated by p53 protein that plays a key role in the regulation of multiple cellular stress responses and prevention of cancerogenesis. Bacterial degradation of p53 was first discovered in the context of *Helicobacter pylori* infection, which is currently the strongest known risk factor for adenocarcinoma of the stomach. This phenomenon, however, is not limited to *H. pylori*, and many other bacterial pathogens inhibit p53 using various mechanisms. Inhibition of p53 by bacteria is linked to bacterial modulation of the host cellular responses to DNA damage, metabolic stress, and, potentially, other stressors.

Various embodiments are directed to expressing anti-aging agents in the microbiome of an individual. By modifying microbes via CRISPR-Cas systems, certain embodiments include the production of low doses of rapamycin and its various analogs as anti-aging agents to treat a multitude of various age-related diseases or disorders. Rapamycin is an inhibitor of mTOR and it is believed to integrate signals from nutrients, mitogenic growth factors, energy, and stress to regulate catabolic and anabolic processes. In response to optimal growth factors and nutrients, mammalian TOR (mTOR) stimulates the cell's synthetic capabilities (such as ribosome biogenesis and protein translation initiation), leading to increases in cell mass and size and accelerates proliferation. Conversely, inhibition of TOR by growth factor withdrawal, nutrient starvation, or stress leads to the down-regulation of high energy-consuming processes and inhibition of proliferation. As such, the TOR pathway is believed to play a significant role in extending lifetimes of individuals. It also has the converse ability to assist in the reduction of cancer growth, given the above referenced Janus face of cancer and aging.

As one of skill in the art will appreciate, given the relationship between bacteria and human mitochondria, it is believed that the modification of an individual's microbiome also has both direct and indirect effects on mitochondrial processes that are important for proper cellular function, including calcium homeostasis, intracellular signal transduction, and the regulation of apoptosis. The process of oxidative phosphorylation for ATP generation in mitochondria is the main source of reactive oxygen species (ROS) within the cell (about 90% of total ROS in cells). Mitochondria are particularly vulnerable to accumulation of damages and when damaged, it leads to increased ROS production and the subsequent accumulation of more mutations. As ROS are highly reactive molecules and can generate diverse damages in the cells, the ROS vicious cycle is believed to account for an exponential increase in oxidative damage during aging. As described herein, it is believed that ROS may be associated with many age-related diseases, for example, diabetes, cardiovascular disease, cancer and Parkinson's disease. The fact that eukaryotes develop a host anti-oxidant defense system also supports the important role of endogenous ROS production, as does the fact that over-expression of superoxide dismutase and catalase extends life span in Drosophila melanogaster. Thus, ROS plays a significant role not only in diseases, such as cancer, but in the overall aging process. Modifying the production of ROS via the alteration of an individual's microbiome is therefore one aspect of the present invention that can be pursued to treat cancer, as well as in furthering the extending of life spans. It is known that mitochondrial integrity declines as a function of age as monitored by decreases in mitochondrial membrane potential, mitochondrial number, and ATP generation. It has also been observed that mice with a dramatic increase in mitochondrial DNA mutations have a shorter life span and exhibit premature aging phenotypes. When TOR is deleted or reduced, life spans are believed to increase. Since cancer cells require unlimited replication potential, all cancers bypass senescence by activating telomerase or alternative telomere lengthening by recombination.

Cancer cells rely on external sources of nitrogen and carbon to grow. Systemic metabolic deregulation promoting tissue wasting and metabolites mobilization ultimately supports tumor growth. Several proinflammatory cytokines promote cachexia: tumor necrosis factor alpha (TNFα), interleukin-6 and -1 (IL-6/IL-1) and interferon gamma. TNFα, initially named cachectin, promotes skeletal muscle wasting mainly through the NF-kB pathway. Cancer patients have increased circulating levels of cytokines (IL-1α, IL-6 and TNFα), suggesting the presence of a robust network of cytokines collectively promoting cachexia. Cachectic muscle features an impaired mitochondrial metabolism associated with ineffective ATP generation. Liver mass substantially increases during cachexia progression, strongly suggesting the involvement of this organ in cancer cachexia. The liver contributes to cachexia by increasing energy expenditure through gluconeogenesis and reducing very low density lipoprotein circulation. It participates as well to the worsening of inflammation by secreting acute phase proteins and reducing albumin secretion, a process mostly driven by IL-6 and TNFα. This eventually results in muscular protein breakdown and adipocytes lipolysis. An interesting feature of cancer cachexia is the progressive switch of fat tissue type, from white (white adipose tissue) to brown (brown adipose tissue), which derives its name from the darker color associated with the enrichment in mitochondria. Babies have far more brown fat than adults, presumably because their growth and development requires the same. Browning of the fat in cancer patients strongly contributes to the increased energy expenditure common in cachectic patients. Fat tissue wasting can be interpreted as a critical turning point in the cachectic process, as it further contributes to the propagation of cachexia by stimulating skeletal muscle wasting. Alteration of the gut flora due to undernutrition and chemotherapy ultimately affects specific metabolite availability and absorption, which in turn affects tumor growth and cachexia. Cancer cachexia is therefore not merely a complication of tumor progression, as cancer cells induce and exploit systemic functions. One aspect of the present invention is to provide an early treatment for cachexia, as it is believed to be eminently treatable at an early stage. The pathogenesis of cachexia in patients at an early stage is where systemic alterations are believed reversible. As cancer cachexia affects different tissue at the same time, the present invention, due to its treatment involving modification and adjustments to an individual's microbiome, is able to provide a unique therapeutic strategy that is able to affect multiple targets. With the understanding that cholesterol production and statin involvement therein is also tied in with mutant p53 cancer affects, the provision of microbes that produce competent p53, that address the cachexia pathways via tomatidine production, and that provide statins to facilitate the halt of cancer growth (while the wild-type p53 can achieve apoptosis of malignant cells), the present invention offers considerable prospects for the treatment of cancer cachexia.

One aspect of the present invention is directed to addressing the bacterial inhibition of p53. Recent studies have found that it is not only viruses, but also some pathogenic bacteria, that actively inhibit p53 and induce its degradation. This phenomenon was initially described in gastric cells co-cultured with *Helicobacter pylori*. *H. pylori* is a gram-negative, spiral-shaped pathogen that lives in the stomachs of approximately half of the world's population. The infection is typically acquired during childhood and causes lifelong chronic infection. Because of the association between *H. pylori* infection and the incidence of gastric cancer, the International Agency for Research on Cancer (IARC) has classified this bacterium as a Group 1 carcinogen. *H. pylori* infection is considered to be the strongest known risk factor for gastric cancer, and epidemiological studies have estimated that, in the absence of *H. pylori*, 75% of gastric cancers would not occur.

*H. pylori* is able to dampen activity of p53 protein by inducing its rapid degradation. One particular aspect of certain embodiments of the present invention is directed to modifying *H. pylori*, preferably via use of a CRISPR-Cas system, such that its abilities to degrade p53 are reduced. The supplantation of such modified *H. pylori*, preferably just after a round of antibiotic treatment to reduce the numbers of native resident *H. pylori* in an individual's body, is done to then provide a competitive advantage of such modified bacteria and thus, will result in the reduction of p53 degradation, assisting in the treatment of the cancerous condition of the individual. Older people with gastric precancerous lesions, who are infected with *H. pylori*, may be particularly vulnerable to degradation of p53. *H. pylori* inhibits p53 through multiple mechanisms, implying that inhibition of p53 activity is an important factor for successful infection. The bacteria not only induce degradation of p53, but also alter the expression profile of p53 isoforms. Other bacteria induce degradation of p53 using a similar mechanism to that of *H. pylori*. As such, the method as set forth herein can be employed with other bacteria, as one of skill in the art will appreciate. For example, the intracellular bacterial pathogen *Chlamydia trachomatis* as well as other *Chlamydia* species, induce degradation of p53 by activating HDM2 protein. Degradation of p53 by *Chlamydia* contributes to cancerogenesis in the female genital tract and inhibition of p53 through the HDM2-dependent mechanism is employed by enteropathogen *Shigella flexneri*, which causes bacillary dysentery in humans. Certain bacteria can inhibit transcription of the p53 gene. Such inhibition of p53 may provide certain benefits to bacteria, such as allowing bacteria to subvert the host cell cycle control and apoptosis mechanisms, resulting in inhibition of cell death and survival of host cells damaged by infection.

The p53 pathway is known to affect immune responses. Among direct transcription targets of p53 are a number of proteins regulating innate immunity and cytokine and chemokine production. p53 is also known to affect NF-κB activity and pro-inflammatory signaling.

One aspect of certain embodiments of the present invention is therefore directed to the role of immunomodulatory function involved in the bacterial inhibition of p53. Some bacteria have evolved to inhibit p53 and do so via multiple mechanisms, including protein degradation, transcriptional inhibition, and post-translational modifications. p53 inhibition affects the host immune response, permitting bacteria to thrive and establish themselves. p53 has a role in controlling the bacterial infections and the inhibition of p53 confers certain selective advantages to bacteria but causes an increase in the risk of tumor development, especially when there exist conditions of prolonged chronic infections.

Numerous bacterial pathogens have also been shown to inactivate p53 during infection. Such inactivation impedes the protective response of the host cell and affects the downregulation of host cell metabolism to interfere with intracellular bacterial replication, highlighting the crucial role of p53 in host-pathogen interactions. Thus, certain aspects of the present invention are directed to providing a microbiome source of competently folded p53, in conjunction with the administration of statins to interfere with the actins of mutant p53, thus providing a way to positively influence infections, especially chronic infections.

Yet other aspects of the present invention are directed to the links between poor oral health and periodontal disease with an increased risk for cancers. The present inventors believe that periodontal disease contributes to the development of systemic inflammation and if left untreated, a chronic, smoldering inflammatory response occurs in response to periodontal microbial pathogens and their products, such as endotoxin. Infection will ultimately stimulate the production of pro-inflammatory cytokines and mediators such as IL-1β, IL-6, TNF-α and MMPs. IL-6, in particular, has tumor-inducing actions, by promoting growth and proliferation, in both healthy and malignant cells. IL-1 promotes tumor growth and metastasis by inducing matrix metalloproteinase activity and other growth factors.

Intestinal bacteria are implicated in several types of cancer. *Helicobacter* species have been associated with enhanced carcinogenesis including liver cancer, colon cancer, and mammary carcinoma. Many human viruses are also known to impair p53 activity. In cervical cancer, the human papillomavirus E6 protein targets p53 for degradation. Bacterial infection has been shown to trigger the p53 pathway and to activate p53 isoforms. Conversely, resveratrol has been shown to inhibit carcinogenesis through the induction of p53-dependent cell death. Thus, certain embodiments involve the modification of one or more microbes that inhabit an individual's microbiome so as to produce desired quantities of resveratrol so as to foster the induction of p53-dependent cell death in cancer situations. Expression of resveratrol in addition to one of rapamycin, tomatidine, p53, etc. in one or more microbes introduced to the microbiome of an individual, whether they be separate microbes or the same, forms another embodiment of the present invention.

In one aspect of the present invention, using CRISPR-Cas, a more stable p53 protein is constructed in terms of the stability of its folding being preserved, thus protecting its tumor suppressing function. According to the present invention, the regions where the p53 protein are most vulnerable to mutations that cause improper folding are therefore targeted and revised so as to impede common mis-folding events. Using such an improved, stable form of p53, and having it expressed in an individual's microbiome, is an important aspect of the present invention as approximately 50% of all human cancers have mutant p53. Tumor initiation and maintenance depend upon inactivation of p53. Thus, certain embodiments of the present invention are directed to a method that restores effective amounts of p53 to a person via an individual's microbiome so that p53 can deter cancer cell proliferation and shrink tumor volume. One way in which to accomplish this objective is to have gut microbes produce amounts of p53 such that effective amounts thereof are available to deter cancers. Another route is to provide a modified version of p53 that is more stable and thus, less susceptible to being degraded by bacteria.

H. pylori modified via CRISPR-Cas to express p53 protein, is one method for ensuring that cancer rates in individuals remain low. The population of an individual's microbiome with such modified bacteria is one way in which to alter the conventional microbiome of the person in a manner that lessens the risk of cancer. As it is known that older people with gastric precancerous lesions, who are infected with H. pylori, may be particularly vulnerable to degradation of p53, the treatment of such individuals with modified H. pylori bacteria can alter the course of various diseases, including cancer. H. pylori inhibits p53 through multiple mechanisms. In the case of H. pylori, expression of the CagA virulence factor is sufficient to inhibit p53 and extend short and long term survival of gastric epithelial cells that have DNA damage. Inhibition of p53 through the HDM2-dependent mechanism is employed by enteropathogen Shigella flexneri, which causes bacillary dysentery in humans. Thus, treatment of such disease states with modified bacteria able to produce desired amounts of competent (e.g. effective, non-mutated, but more stable p53 proteins) is one aspect of the present invention. In addition to cancer treatments, the modification of certain bacteria to address the levels of p53 expressed thereby is an important aspect of various embodiments of the present invention. For example, down-regulation of p53 protein has been reported in studies of Neisseria gonorrhoeae, which is responsible for the sexually transmitted gonorrhea that may increase the risk of genital neoplasms. N. gonorrhoeae causes strong genotoxic stress and induces both single and double strand DNA breaks, which is believed to be associated with and can inhibit transcription of the p53 gene.

The p53 pathway is known to affect immune response and among direct transcription targets of p53 are a number of proteins regulating innate immunity and cytokine and chemokine production. p53 is also known to affect NF-κB activity and pro-inflammatory signaling. One aspect of certain embodiments of the present invention therefore involve the role of immunomodulatory function involved in the bacterial inhibition of p53 which affects the host immune response and permits bacteria to thrive.

In certain embodiments, the use of CRISPR-Cas is employed to achieve targeted gene deletion for tailoring bacteria for cancer therapy. The above discussion with respect to modifying p53 protein production, e.g. so as to render p53 proteins more stable and less susceptible to degradation, is an example of how CRISPR-Cas systems can be employed to achieve this objective. A bacterial strain is preferably designed by the use of CRISPR-Cas systems in a way that the microorganism is both attenuated and optimized at the same time. For example, auxotrophic/attenuated bacteria may express a complementing gene under an inducible promoter, such that their activation depends on presence of, for example, arabinose or anhydrotetracycline, and thus, such bacteria can be inducibly complemented.

In some embodiments, Gram-negative bacteria, like Salmonella, are employed as active delivery vehicles and preferably, instead of depending upon lysis to deliver the contents of the bacterium, a controlled release of a therapeutic compound is facilitated in a manner that achieves continuous expression and release of a therapeutic compound (e.g. such as tomatidine or p53) with a desired high concentration over a period of time to effect cancer reduction, muscle atrophy treatment, etc. One objective is to deliver therapeutic compounds actively and directly to the site of interest by using bacteria of the individual's inherent microbiome. Thus, one aspect of the present invention is directed to the exploitation of the unique tumor colonizing property of bacteria to achieve drug delivery via bacterial mediated tumor therapy. In certain preferred embodiments, use of bioluminescent bacteria are employed to follow the course of the microorganisms into the tumor. While applicable for a number of cancers, in one embodiment, a CRISPR-Cas modified bacterium is used in the treatment of pancreatic cancer with Listeria monocytogenes. Thus, in certain embodiments, bacteria are designed to deliver therapeutic compounds like chemotherapeutic drugs directly into the cancerous tissue. In various embodiments, bacteria that reside in an individual's microbiome (e.g oral, gut, vaginal, skin, etc.) are employed as vector systems that provide therapeutic compounds to cancer sites, including solid tumors and in a manner that is far more efficacious than, and that overcomes, the limitations of conventional therapies.

Yet another example of cancer treatments employed using the present invention is the treatment of esophageal adenocarcinoma (EA), which has increased 6-fold in the U.S. since the 1970s, as well as pancreatic cancers. No one knows why. High antibody levels for one of the more infectious periodontal bacterium strains of Porphyromonas gingivalis have been associated with a two-fold risk for pancreatic cancer. Individuals with high levels of antibodies for some kinds of harmless "commensal" oral bacteria were associated with a 45-percent lower risk of pancreatic cancer. Thus, one aspect of the present invention is directed to the reduction in pancreatic cancer via modification of an individual's microbiome, and in particular their oral and gut microbiomes. Administration of modified oral and gut bacteria having desired characteristics as described herein is one way in which to reduce the incidence of pancreatic cancer.

Yet another aspect of the present invention is directed to the use of human specific species of bacteria that are then modified to enhance one or more characteristics deemed beneficial to the microbiome of an individual, including bacteria that have been modified via a CRISPR-Cas9 and/or Cp11 systems to either repress the expression of a particular protein or lipid, or to increase the production of beneficial microbial secretions, including but not limited to tomatidine and p53 protein. Expression of genes that encode statins may also form the basis of other embodiments such that the positive effects of statins on addressing the action of mutant p53 on cancer growth can be addressed. Other embodiments employ the cholesterol-busting drugs Repatha or Praluent, which presently are the only approved Proprotein convertase subtilisin kexin type 9 (PCSK9) inhibiting therapies on the market, which may complement the use of generic cholesterol treatments like statins as described herein in addressing mutant p53 oncogenic effects. Still other embodiments employ the microbiome administration of pegfilgrastim, a human-engineered protein that stimulates the production of neutrophils.

One objective of such embodiments is to avoid modifying an individual's human genome in order to treat a disease state. One can avoid modifying the human genome and still significantly affect the health of humans by instead employing modifications to the skin, oral and gut microbiomes. Use of human specific strains of bacteria, whether they are commensal or pathogenic, including bacteria that are modified to alter their native pathogenicity, is one preferred aspect of many embodiments of the present invention. In particular, in view of the tropism demonstrated by S. pyogenes for humans, and the recognition that such bacterial species is found in both the oral and skin microbiome of humans, *S. pyogenes* is a preferred bacterial species to employ in various embodiments of the present invention to treat various disease states.

In various embodiments, re-cultivated human intestinal microbiota obtained by cultivation of a stool sample in a cultivation medium is employed to promote the proliferation of select bacteria, including at least two of the following Phyla: *Bacterioidetes, Firmicutes, Proteobacteria* and *Actinobacteria*, and more preferably at least two of the following: *Faecalibacterium, Lachnospira, Veillonella, Rothia; Lactobacillus johnsonii* and *Prevotella*. In other embodiments, one or more of the following microorganisms is employed: *Bifidobacterium lognum, B. infantis* BCRC 14602 *Prevotella; Ruminococcus, Bifidobacterium infantis, Lactobacillus acidophilus, Bacteroides fragilis, B. longum* bv. *Infantis* isolate UCD272p; *B. infantis* BCRC; *B. longum* bv. *Infantis*, AY 151398; and *Lactobacillus ruminus; L. lactis, L. lactis cremoris, L. plantarum*, and *L. raffinolactis; Faecalibacterium, Lachnospira, Veillonella*, and *Rothia; Lactobacillus johnsonii, Lactobacillus crispatus, Lactobacillus brevis, Lactobacillus buchneri, Lactobacillus casei, Lactobacillus delbrueckii, Lactobacillus fermentum, Lactobacillus helveticus, Lactobacillus kefir, Lactobacillus paracasei, Lactobacillus plantarum, Lactobacillus rhamnosus, Lactobacillus salivarius, Streptococcus thermophilus, Lactococcus lactis, Lactococcus plantarum, Lactococcus raffinolactis, Leuconostoc lactis, Leuconostoc mesenteroides, Enterococcus faecalis*, and *Enterococcus faecium; Enterococcus faecalis; Lactobacillus reuteri*, and *Lactobacillus paracasei*. In certain embodiments, the method includes the use of a mixed culture of bacterial cells of three to eight species of lactic acid bacteria. In particular mixed cultures, the following may be included: *Saccharomyces cerevisiae, Lactobacillus delbrueckii, Lactobacillus acidophilus, Lactobacillus plantarum, Lactobacillus fermentum, Lactobacillus casei, Lactobacillus rhamnosus, Lactococcus lactis* and *Streptococcus thermophilus; Enterococcus faecium; Bacillus coagulans; Leuconostoc, Pediococcus, Lactobacillus casei, Lactobacillus plantarum, Lactococcus lactis* subspecies *lactis, Lactococcus lactis* subspecies *cremoris; Lactobacillus plantarum; Pediococcus pentosaceus; Streptococcus thermophilus; Lactobacillus paracasei; Lactobacillus plantarum, Lactobacillus gasseri* and *Lactobacillus salivarius; Lactobacillus acidophilus* PM-A0002, *Lactobacillus gasseri, Lactobacillus salivarius, Lactobacillus acidophilus* PM-A0013; *Leuconostoc mesenteroides; Lactobacillus bulgaricus, Lactobacillus rhamnosus, Lactobacillus acidophilus, Lactobacillus paracasei; Bifidobacterium bifidum; Lactobacillus brevis; Enterococcus durans, Leuconostoc mesenteroides; Lactobacillus crispatus*. Still other embodiments of the invention may comprise extracts obtained from one or more of the following species: *Lactobacillus fermentum, Lactobacillus rhamnosus, Lactobacillus plantarum, Lactobacillus johnsonii, Lactobacillus helveticus, Lactobacillus casei defensis, Lactobacillus casei* ssp. *casei, Lactobacillus paracasei, Lactobacillus bulgaricus, Lactobacillus paracasei, Lactobacillus acidophilus, Lactobacillus reuteri, Lactobacillus salivarius*, and *Lactobacillus lactis*. In some embodiments, at least one strain from each of the above species of bacteria is used, while in other embodiments, one or more specific strains from the list above may be removed or substituted with one or more different strains. In particular, some embodiments of the present invention comprise an extract obtained from one or more of the following bacterial strains: *Lactobacillus fermentum* 1-3929, *Lactobacillus rhamnosus* 71.38, *Lactobacillus plantarum* 71.39, *Lactobacillus johnsonii* 103782, and *Lactobacillus helveticus* 103146; *Lactobacillus fermentum* 1-3929, *Lactobacillus rhamnosus* 71.38, *Lactobacillus plantarum* 71.39, *Lactobacillus johnsonii* 103782, and *Lactobacillus helveticus* 103146. The following bacteria species may also be employed: *Lactobacillus acidophilus* PM-A0002 deposit number M 207038, *Lactobacillus gasseri* PM-A0005 deposit number M 207039, *Lactobacillus salivarius* PM-A0006 deposit number M 207040, *Lactobacillus johnsonii* PM-A0009 deposit number M 207041 and *Lactobacillus acidophilus* PM-A0013 deposit number M207042. Certain other embodiments of the present invention include a combination of particular bacterial strains, selected from the group consisting of *Prevotella; Lactobacillus johnsonii; Bacteroides fragilis, Lactobacillus ruminus*, and at least one of *B. longum* bv. *Infantis* isolate UCD272 or *B. longum* bv. *Infantis*, AY 151398. In more preferred embodiments, the gut microbiome of an individual is modified by providing in preferably a pill form a collection of microbes that include at least two of the following Phyla: *Bacterioidetes, Firmicutes, Proteobacteria and Actinobacteria*, and more preferrably at least two of the following: *Faecalibacterium, Lachnospira, Veillonella, Rothia; Lactobacillus johnsonii* and *Prevotella*.

To comply with written description and enablement requirements, the following references are incorporated herein for their disclosures of particular strains that can be employed in various embodiments of the present invention: 2014/0349405 to Sontheimer; 2014/0377278 to Elinav; 2014/0045744 to Gordon; 2013/0259834 to Klaenhammer; 2013/0157876 to Lynch; 2012/0276143 to O'Mahony; 2015/0064138 to Lu; 2009/0205083 to Gupta et al.; 201/50132263 to Liu; and 2014/0068797 to Doudna; 2014/0255351 to Berstad et al.; 2015/0086581 to Li; PCT/US2014/036849 and WO 2013026000 to Bryann; U.S. Pat. Publication No. 2015/0190435 to Henn; 2012/0142548 to Corsi et al.; U.S. Pat. No. 6,287,610, U.S. Pat. No. 6,569,474, US2002/0009520, US2003/0206995, US2007/0054008; and U.S. Pat. No. 8,349,313 to Smith; U.S. Pat. No. 9,011,834 to McKenzie; 20150004130 to Faber et. al, 20160206666 to Falb; 20160206668 to Kort et. al; and WO2015069682A2 to Asesvelt, et. al.

As one of ordinary skill in the art will appreciate, one must give value to their existence by behaving as if one's very existence were a work of art. You must have chaos within you to give birth to a dancing star. And those who were seen dancing were thought to be insane by those who could not hear the music. To live is to suffer, to survive is to find some meaning in the suffering. No one can construct for you the bridge upon which precisely you must cross the stream of life, no one but you yourself alone. There will always be rocks in the road ahead of us. They will be stumbling blocks or stepping stones; it all depends on how you use them. The center is everywhere. Bent is the path of eternity. Long-live the memory of Doug Scott.

In still other embodiments, interspecies interactions within mixed microbial communities is involved, with the objective being to modify competitive relationships involving nonbiocidal biosurfactants, enzymes, and metabolites produced by bacteria and other microorganisms in a manner such that selection of particular bacterial species can be employed to do one or more of inhibit initial adhesion, trigger matrix degradation, encourage jamming of cell—cell communications, and induce biofilm dispersion. Nonbiocidal molecules are thus employed to modify competitive interactions within biofilms in a manner that promotes the overall health of an individual's microbiome.

In certain embodiments, particularly designed to address the proper developmental biology of a human's immune system, so important in early and later life ability to thwart cancerous conditions, a bacterial formulation is applied to newborns within a critical window of time after birth, preferably within the first 24 hours of the newborn's birth, more preferably within 6 hours of their birth, even more preferably within 3 hours of birth, and most preferably within an hour after their birth. The administration can be by several methods, but preferably is a lotion, ointment or gel that is rubbed onto the newborn's skin, preferably all over his/her entire body. A spray or mist can also be applied that contains the bacterial and microbe formulations as set forth herein. While not bound by theory, the critical window to apply to the newborn's skin the referenced formulations, e.g. microbial mixtures of bacteria beneficial in triggering immune system development as further described herein, is within a relatively short time period and is necessary to establish immune tolerance to a variety of commensal microbes. The manner in such and the content of microbes presented at a time in which a newborn has his/her skin, oral cavity and gut microbiome colonized establishes immune tolerance to particular commensal microbes. The influx of highly activated T cells into neonatal skin and gut is believed to occur in such critical window. So a mother of a newborn has a choice: to simply rely upon chance as to what particular microbes might be present during this critical window of the newborn's establishing immune tolerance to particular bacteria and other microbes; or to provide the newborn with a selected formulation containing predetermined microbes such that the newborn's developing immune system can properly react to the microbes in the predetermined formulation, and thus provide the newborn with the opportunity to develop a more expansive immune tolerance profile. The mechanism that promotes tolerance is tissue specific, and thus, the skin, oral cavity and the gut may have different ways by which to mediate tolerance to commensal microbes. For example, to establish a healthy status of a newborn's skin as it relates to commensal microbes on its skin, the particular type of microbes, including bacteria, brought into contact with his/her skin is achieved in a certain time period after birth (e.g. within 1 to 24 hours after birth) so that the developing immune system of the infant establishes tolerance to such microbes, thus avoiding allergies, autoimmune diseases and other related diseases, as well as chronic inflammation of the skin.

In certain embodiments of the present invention, the skin/oral and gut microbiome is enhanced via providing microbes able to metabolize lipids, proteins and carbohydrates, and thus, with respect to the skin microbiome, produce acid that aids in maintaining the so-called "acid mantel" of the skin. In preferred embodiments the bacteria that is modified has a very narrow host tropism, such that the bacteria are specific for the human species and thus, their modification poses little if any risk to other animals or organisms.

Other embodiments are directed to combating infections of a person's skin by the bacteria *Staphylococcus aureus*. Patients with malignancies represent a population at high risk for drug-resistant infections. *S. aureus* is a significant cause of morbidity and mortality in pediatric oncology patients. *Staphylococcus aureus* is a commensal and pathogen of both humans and cattle. In certain embodiments the accessory gene regulator (Agr) system and the virulence regulation of *S. aureus* pathogenesis is modified to delete or to at least reduce the virulence of the bacteria. In such a way, the present invention provides a way to effectively combat *S. aureus* infections. In various embodiments of the present invention, CRISPR-Cas9 and/or Cp11 systems are employed to render ineffective the virulence factors of such bacteria involved with the establishment and propagation of infection. Other embodiments involve the modification of such bacteria to express desired amounts of tomatidine, p53, rapamycin, etc. as otherwise described herein. Several molecules have been found to interfere with *S. aureus* virulence regulation, especially those targeting the Agr quorum-sensing signaling molecule. By modification of this bacterial species using CRISPR-Cas and/or Cp11 it is possible to achieve broad-spectrum inhibitory effects on most *S. aureus* strains and Agr subtypes.

The tropism of individual bacteria for particular host tissues (e.g., skin vs. respiratory tract vs. gastrointestinal tract) is determined by the array of available adhesion-receptor pairs. In preferred embodiments, bacteria having substantial, if not entire, human host specificity are employed. For example, *Salmonella enterica* serovar *Typhi*, known to be the bacteria responsible for typhoid fever, a life-threatening human disease, demonstrates strict human host specificity. In certain embodiments, the virulence factors of such bacteria are compromised by being modified via the CRISPR-Cas or Cp11 system to render the modified bacteria as non-pathogenic. This is not dissimilar to the modification of BCG from its virulent parentage form a tuberculosis causing bacterium, and one of skill in the art will appreciate the varous ways to arrive at an appropriate attenuated microbe for use in various aspects and embodiments of the present invention. Similarly, the bacteria *Neisseria*, the causative agent of gonorrhea, is a disease restricted to humans, and thus similar CRISPR-Cas and/or Cp11 systems may be employed to reduce if not eliminate the virulence factors of such bacteria. Likewise, *Helicobacter pylori* is known to be an etiologic agent of gastritis and peptic ulcer disease in humans. The iron acquisition system of *H. pylori* by the human lactoferrin receptor system is believed to play a major role in the virulence of H. pylori infection. The CRISPR-Cas and/or Cp11 systems may be employed to reduce if not eliminate the virulence factors of this bacteria. Yet another bacteria demonstrating human tropism is *Haemophilus influenza*, a Gram negative species that requires heme and has exclusive human host specificity. The precise way in which to employ CRISPR-Cas systems is relatively straightforward and is described in great detail in various references that are incorporated herein for written description and enablement purposes. In certain embodiments, the CRISPR-Cas and/or Cp11 systems may be employed to reduce if not eliminate the virulence factors of such bacteria. The distinction between throat and skin group A *Streptococcus* has become blurred and to date there have been few advances in treatment of group A *Streptococcus* skin infections. Certain aspects of the present invention include the modification of skin group A *Streptococcus* to reduce the likelihood, if not prevent, related skin diseases, including eczema, atopic dermatitis, acne, allergic inflammation, skin hypersensitivity, UV-induced skin damage, skin cancer.

The present invention in various embodiments is directed to a variety of consumer products including cosmetic products such as skin care products (bath preparations, skin washing and cleaning products, skin care products, eye cosmetics, lip care products, nail care products, intimate hygiene preparations, foot care), those with special effects (sunscreens, tanning agents, deodorants, anticholinergics, depilatories, shaving, fragrance), those for oral or dental hygiene and those for hair care (shampoos, conditioners, etc.) One objective of the present invention is to achieve various health and cosmetic benefits by providing a healthy, balanced skin, oral and gut microbiome. Other embodiments are directed to prebiotic agents for use with those microbiomes. In preferred embodiments, CRISPR-Cas and/or Cp11 modified bacteria, especially those demonstrating total or substantial tropism for humans, are employed in one or more of the above referenced products, with certain features, namely, virulence factors, reduced or attenuated, if not eliminated. In such a manner, there is a competitive inhibition of undesired bacteria with the modified bacteria as set forth herein.

In certain embodiments, the cleansing of one's skin to effectively reduce by at least about 50%, more preferably about 30%, and most preferably to reduce by at least about 25% of native bacteria on an individual's skin portion to be addressed, is performed prior to purposefully contacting the individual's skin with one or more bacteria species that have been modified via employment of a CRISPR-Cas and/or Cp11 system to reduce if not effectively compromise the virulence factors of such bacteria, and more preferably a bacteria that has a host specificity exclusive to humans. Similarly, treatment of the oral and gut microbiome can be addressed by such an initial reduction in the native bacterial and other microbe populations of an individual, followed by repopulation of such microbiomes with desired modified bacteria, especially those modified via CRIPSR-Cas systems.

The adherence to the skin of problem flora, such as pathogenic bacteria and yeast, has been associated with numerous ailments, including skin infections, diaper rash, urinary or vaginal infections, and malodors. Various products are commercially available to clean the surface of skin and to remove problem flora therefrom. Many presently available products include an antibacterial agent, such as an organic acid, which can be used in combination with the surfactant to kill bacteria located on the skin's surface. Also, various antibacterial soaps and cleansers are available to cleanse hands and kill flora adhered to the skin's surface. These antibacterial soaps are generally highly effective in killing bacteria located on the skin.

Various embodiments of the present invention stand in contract to accepted methods of dealing with skin and bacteria issues (which largely solely involve killing bacteria, etc—such as described in Kimberly Clark's U.S. Pat. No. 8,110,215 to Koenig, et al.) In contrast, various embodiments of the present invention are directed to modification of various bacteria on a person's skin (and in still other embodiments to the gut and oral microbiome) so as to reduce the pathogenicity thereof and to rely upon competitive inhibition of such modified bacteria on the skin to further reduce the presence of pathogenic bacteria on an individual's skin. In one particular embodiment, the topical administration of statin compounds on skin cancers is done to address the negative effects of mutant p53. In concert with the administration of bacteria on the skin that are able to produce competently folded, wild-type p53, the employment of topical statin compounds is believed to offer an extremely effective anti-cancer preparation that can arrest the growth of skin cancers. Other embodiments employ the administration of statins via the film strips as otherwise described herein, especially in the form of mucosal adhesive strips that can be used to administer statins in a concentrated form to a tissue contacted by such a strip. Most statins exhibit antimicrobial effects against various oral microorganisms. Simvastatin is most effective against the periodontal pathogens *Aggregatibacter actinomycetemcomitans* and *Porphyromonas gingivalis*, and against most dental plaque bacteria, including *Streptococcus mutans*. Statins also exhibit antiviral properties against human cytomegalovirus, hepatitis B virus, and hepatitis C virus, and have antifungal properties against *Candida albicans, Aspergillus fumigatus*, and *Zygomycetes* spp. Use of statins in a topical administrative form, especially via a strip that can be used in a perosn's mouth to address and treat oral cancers, is one of several embodiments of the present invention. Such strips preferably further comprise either p53 proteins, or bacteria that produce such p53 proteins, such that anti-cancer treatments can be delivered directly to mucosal tissue in a fashion that addresses the neutralization of mutant p53 (e.g. by the actions of topically administered statins) and by the positive anti-cancer effects of wild type p53. Various embodiments thus employ statins to ameliorate different inflammatory diseases, as well as cancer, and especially skin cancers, as well as other acute and acquired diseases either mediated or not mediated by cholesterol.

As for lotions of the present invention, in preferred embodiments, there is an objective to limit if not preclude the use of phthalates, which are extremely toxic and are believed to also be human carcinogens. Thus, in preferred embodiments of the present invention, such lotions do not employ such toxic agents, and in particular, agents toxic to bacterial species for which the inventors suggest be used, e.g. those modified to reduce pathogenicity, virulence factors, etc., so as to establish a population of such modified bacteria on a person's skin, and in such a manner, reduce the incidence of skin infections and diseases. Thus, lotions, creams, gels, etc. that include such toxic agents, including but not limited to phthalates, are not employed, but rather, lotions that provide an environment for the bacteria as set forth herein to survive and to thus be available to provide benefits to the skin of individuals to which they are applied, are particularly preferred.

Healthy, normal skin exhibits a slightly acidic pH in the range of 4.2-5.6, which aids in the prevention of pathogenic bacterial colonization, regulation of enzyme activity, and maintenance of a moisture-rich environment; however, after the age of 70, the pH of skin rises significantly, stimulating protease activity. Thus, one objective of several embodiments of the present invention is directed to lowering the pH of the skin of an individual, especially those at about the age of 70, so as to encourage a skin environment conducive to the proliferation of one or more bacteria that have been modified to promote skin health and to reduce the ability of undesired bacteria from colonizing the skin of the person. Probiotic metabolism frequently produces acidic molecules, lowering the pH of the surrounding environments seen with Lactobacilli producing free fatty acids (FFAs) and conjugated linoleic acid (CLA) during the fermentation process. Thus, the use of probiotics is employed to restore the normal skin pH and consequently return protease activity levels closer to those seen in young, healthy skin.

The main microbes that reside on human skin can be divided into four phyla: *Firmicutes, Actinobacteria, Proteobacteria*, and *Bacteroidetes. Staphylococcus* spp. and *Corynebacterium* spp. are the dominant bacteria at the genus level. Significantly fewer *Corynebacterium* spp. have been observed in cachexia patients compared to healthy subjects. The presence of cancer and cachexia alters human skin bacterial communities. Understanding the changes in microbiota during cancer cachexia has led to new insights into the syndrome. Especially with tomatidine enhanced bacteria, the provision of such modified bacteria to a person's microbiomes, including the gut, oral and skin microbiomes, provides a way to address numerous issues arising from cancer cachexia.

Competitive inhibition is relied upon in various embodiments of the present invention to advance the repopulation of skin, oral cavity and gut environments with beneficial microbes. For example, and using the skin microbiome as one specific case, in one embodiment, repopulating an individual's skin with beneficial bacteria, preferably in balanced percentages and having preferred species provided, can be used in conjunction with an antimicrobial composition. Preferably, an antimicrobial is first administered to suppress or eradicate the resident populations of bacteria on a person's skin, including any abnormal organisms or pathogenic bacteria, then the normal flora is repopulated by the administration of at least one of the modified bacteria as described herein, including those modified using CRISPR-Cas and/or Cp11 systems to delete certain portions of genes or to add certain genes to facilitate the colonization of a person's skin with beneficial bacteria that maintain the general health of a person's skin.

The term "therapeutically effective amount" as used herein means the amount contained in the composition administered that is of sufficient quantity to achieve the intended purpose, such as, in the case of cachexia, an amount that is able to reduce muscle wasting activities that cause a loss of muscle weight in an individual.

It is preferred in many embodiments that antimicrobial treatments are completed before the administration of modified bacteria—selected as being desirable to maintain skin, oral or gut microbiome health, including but not limited to modified bacteria of the following: *Firmicutes* (mainly *Streptococcus* and *Staphylococcus*) and *Actinobacteria* (mainly *Corynebacterium* and *Propionibacterium*). By employing such modified bacteria, one is able to establish and maintain the reduction if not preclusion of various skin diseases, including skin cancer. One objective of certain aspects of the present invention is to provide a method and system that, by using health promoting strains from the microbiome in topical probiotics, it is possible to treat and to further reduce the risk of skin cancer. One of skill in the art will appreciate similar objectives in the treatment of the oral and gut microbiomes for diseases that affect the same.

Repair of tissue wounds is a fundamental process to re-establish tissue integrity and regular function. Infection is a major factor that hinders wound healing. Multicellular organisms have evolved an arsenal of host-defense molecules, including antimicrobial peptides (AMPs), aimed at controlling microbial proliferation and at modulating the host's immune response to a variety of biological or physical insults. Certain embodiments of the present invention are directed to the use of AMPs as endogenous mediators of wound healing. Thus, one aspect of several embodiments of the present invention is directed to genetically manipulating bacterial species native to the skin. *Staphylococcus epidermidis*, which is found in abundance on human skin, can cause immune tolerance in some—but in others, inflammation and activation of T cells against the bacteria. The present inventors submit that the immune system may set up tolerance to commensal bacteria only early in life, during a time where there is an influx of regulatory T cells unique to the skin, e.g. during the first week after birth. This colonization of the skin by regulatory T cells—immune cells that dampen the responses of effector T cells—is believed to be required for tolerance to *S. epidermidis*. There is an abrupt wave of regulatory T cell infiltration into neonatal skin that occurs at a defined period and this window dictates the achievement of commensal-specific tolerance.

One aspect of the present invention is directed to the introduction of tolerance to commensal bacteria during the time the developmental window is still open, thus providing the individual with life-long protection from a variety of diseases. Still other embodiments, however, are directed to introducing tolerance following the closing of the developmental window, e.g. after the first week after birth, so that individuals can purposefully be induced to have commensal-specific tolerance as an adult. Understanding which microbes cause infection and which are tolerated and the critical time frames where the immune status is set is one aspect of the present invention.

Skin bacterial communities are influenced by ethnicity, lifestyle and/or geographic location. Skin bacterial communities that are particularly employed in the modifications as set forth herein include: *Firmicutes, Proteobacteria* and *Actinobacteria*); *Firmicutes* (mainly *Streptococcus* and *Staphylococcus*) and *Actinobacteria* (mainly *Corynebacterium* and *Propionibacterium*), while still other preferred bacteria include *L. acidophilus* NCFM, *L. salivarius* Ls-33, *Bifidobacterium lactis* 420, *L. acidophilus* La-14 and *Propionibacterium jensenii* P 63.

In various embodiments, cosmetics are provided that provide for a medium favorable for maintaining a desired physico-chemical balance of the skin without favoring the development of pathogenic microorganisms. To achieve this objective, certain oligosaccharides that are metabolized by several beneficial strains of the skin microflora, such as *Micrococcus kristinae, Micrococcus sedentarius, Staphylococcus capitis, Corynebacterium xerosis* and *Lactobacillus pentosus*, are employed in formulations, in conjunction with one or more of the modified bacteria as described herein, including those modified to produce tomatidine and/or p53 proteins.

Pathogenic strains such as *Staphylococcus aureus, Gardnerella vaginalis* and *Propionibacterium acnes* do not typically metabolize, or very slightly metabolize, certain oligosaccharides. In certain embodiments, sugar sources are provided in amounts and in association with beneficial bacteria, whether they be those modified as described herein, or those that are naturally non-pathogenic in nature, so as to achieve the colonization of the skin in a fashion to provide the health benefits sought.

Yet another aspect of the present invention is directed to the treatment of brain cancer, which is the leading cause of cancer-related death in patients younger than age 35 and accounts for roughly 10% of all cancers diagnosed in North America. Treatment of brain tumors is complicated by the fact that there are more than 120 different types, which range from low grade astrocytomas to high grade glioblastomas (GBM). Malignant gliomas, such as GBM, are by far the most common brain cancer found in adults and one of the most difficult to treat. Even with aggressive single and multimodal treatment options such as surgery, chemotherapy, radiation and small molecule inhibitors, the survival has remained unchanged over the past three decades with a median survival of less than one year after diagnosis. Reasons for the failure of conventional treatments is multifactorial including the highly infiltrative/invasive nature of GBM, limitation of drug delivery through the blood brain barrier and neural parenchyma, and genetic heterogeneity resulting in intrinsic resistance to available treatments and the rise of aggressive resistant clones.

To address such brain tumors, one aspect of the present invention is directed to the delivery of tomatidine and/or p53 directly to tumors through interstitial therapy, where a surgeon implants small e.g. dime-sized strips having the agent as desired, e.g. tomatidine, statins, p53, etc. and the preferably biodegradable strips that comprise such agents are delivered directly into the tumor so that they may release desired concentrations of the agent(s) locally over a period of days or weeks, prior to safely dissolving. Such strips can be customized to treat a variety of solid tumor disease of the breast, lung, colon, kidney and skin. The inventors incorporate by reference various novel technologies relating to the use of strips, such as oral strips as described in U.S. Pat. No. 9,010,340 and Ser. No. 14/611,458. One of skill in the art will appreciate the modifications to such strips to employ their use in the various cancer treatment regimens as described herein.

In one particular aspect of the present invention, the Zika virus is employed in the treatment of brain cancer due to its ability to target human brain cells. Employing such targeting in combination with the other aspects of the present invention as described herein, including the production of tomatidine, statins, rapamycin and/or p53 by microes in an individual's microbiomes, offers new hope for an effective treatment of particular brain cancers. Zika virus is a member of the *Flaviviridae* family, which includes West Nile Virus, St. Louis encephalitis virus, Kunjin virus, yellow fever virus, Dengue virus, and Japanese encephalitis virus. Cellular apoptosis and necrosis follow infection for many of these viruses, and appears to be dependent upon several factors, such as viral load, host factors, and specific viral protein induced apoptosis/necrosis pathways, many of which have yet to be fully defined. The expression of BAX is regulated by the tumor suppressor p53. The majority of BAX is found in the cytosol, but upon initiation of apoptotic signaling, BAX undergoes a conformational shift and becomes mitochondrial membrane associated.

Still another aspect of the present invention is directed to the use of particular mushroom or fungi extracts to combat cancer, especially when combined with tomatidine to address the muscle atrophy commonly associated with cancer. Use of particular compounds derived from mushrooms, especially those produced by modified bacteria resident in an individual's microbiome and that are provided via the use of CRISPR-Cas systems, is a new way to address treatment of many cancer types. For example, the small-molecule neoalbaconol (NA) from *Albatrellus confluens* possesses the ability to inhibit cell growth of many cancer cells. Cholangiocarcinoma (CCA) is a lethal malignancy with poor prognosis that makes up 10-25% of all primary liver cancer diagnosed worldwide. *Albatrellus confluens*, mainly distributed in Southwest China, is a member of the *Polyporaceae* family. Several compounds with anticancer potential have been isolated from this fungus and NA has proven to be efficacious in inhibiting the growth of a broad spectrum of tumor cell lines. Dosage administration for mice would be NA treatment (100 mg/kg/day)—and thus, for humans, would be commensurate with the person's size being treated. When combined with tomatidine, an effective treatment for cancer and one that addresses muscle atrophy associated with cancer. Preferably, at least about 5 mg of tomatidine every day is provided to an individual via the production thereof by gut microbes in such individual. Systemic administration of one or more disclosed compounds (e.g., by parenteral injection or by oral consumption) can be used to reduce fat, increase the muscle to fat ratio, increase the muscle mass and reduce the fat, and prevent an increase in fat in an animal.

It is known that most human viruses impair p53 activity. For example, in cervical cancer, the human papillomavirus E6 protein targets p53 for degradation. Bacterial infection triggers the p53 pathway and to activate p53 isoforms and the p53 R249S variant is often observed in liver cancer as being associated with aflatoxin B1 food contamination. In one aspect of the present invention, CRISPR tools are employed to insert into cancer cells particular sequences that encode for the expression of toxins that treat such cancers, preferrably in conjunction with the provison of p53, statins, etc. as explained herein. Appropriate promoters may be used to then "turn on" the expression of such genes, thus enabling amounts of toxins to be made by the cancer cell, destroying itself. In other words, this is similar in concept to "infecting" a cancer cell with a particular DNA or RNA insert, whether in the nuclear DNA or in the mitochondrial DNA (or RNA of the cell) and by activating promoters to effectively "turn on" the production of the protein (e.g. a toxin), one can control the destruction of the cell. Similarly, stretches of DNA can be inserted into cancer cells such that when a later infection with a predetermined bacterial species occurs, the normal immune response of the individual's resident immune system will target such DNA stretches, and the targeting step itself can be used to provide the cancer cells with suitable components that ultimately reduce the growth of cancerous tissue and/or kill such cells. Other systems employ CRISPR tools to ensure that cancer cells, when attempting to counter the infection by a virus, results in turning on destructive machinery that selectively kills the cancer cell in the process.

Yet other embodiments, directed to the treatment of throat cancers, employ factors of the disease causing bacteria *Streptococcus pyogene*. For example, in one embodiment, the hyaluronic acid capsule of *Streptococcus pyogenes*, along with its M proteins, which are a major factor behind its virulence due to their role in the attachment to host tissues. Host immunity to *Streptococcus pyogenes* results from the development of antibodies specific to M protein and the hyaluronic acid capsule of *Streptococcus pyogenes* is chemically similar to human connective tissue, which allows it to go unrecognized as an antigen by the host's body. Adhesion of *Streptococcus pyogenes* to the host cell is the first step in pathogenesis, and the invasion process into the host cells takes place in very short order. *S. pyogenes* adhesion to human cells depends on the presence of cell surface adhesions including the M protein. The cell wall associated M protein is a major virulence factor of *S. pyogenes*, which can bind directly to the extracellular matrix components (e.g. fibrinogen). *S. pyogenes* possesses an arsenal of countermeasures against attacks from the host, including resistance of phagocytosis that is mediated by the hyaluronic acid capsule.

In various embodiments of the invention as described herein, components of CRISPR-Cas systems are involved in the regulation of bacterial gene expression. As Cas proteins have proven to be great biotechnology tools, these novel functions are used in various embodiments of the present invention for gene regulation of bacteria that comprise the human microbiome. In particular, a particular class of riboswitches, called thermosensors can sense temperature changes and can be used effectively with especially gram positive bacteria, in contrast to Gram negative bacteria, which use translational attenuation.

Still another aspect of the present invention is directed to the production of rapamycin, a small molecule drug derived from *Streptomyces hygroscopicus*, by bacteria in a person's microbiome. Much of the role and function of mTOR has been ascertained with rapamycin, a known macrolide antibiotic produced by *Streptomyces hygroscopicus*. The mechanistic target of rapamycin (mTOR) is an evolutionarily conserved serine/threonine kinase that is ubiquitously expressed in immune cells. mTOR integrates multiple environmental signals to regulate diverse cellular processes including protein translation, cell growth, proliferation, metabolism, migration, and survival. Bacterial pathogens including *Listeria monocytogenes* (*L. monocytogenes*) and *Staphylococcus aureas* can also activate mTOR to promote IL-10 production and increase their survival in the host. Rapamycin is an immunosuppressant drug used to prevent activation of T cells and B cells by inhibiting their response to interleukin-2 (IL-2). Its mode of action is to bind the cytosolic protein FK-binding protein 12 (FKBP12), and the sirolimus-FKBP12 complex in turn inhibits the mammalian target of sirolimus (mTOR) pathway by directly binding the mTOR Complex1 (mTORC1).

Checkpoint inhibition, namely PD1/PD-L1 pathway inhibition, has shown impressive results in many tumor types. One aspect of the present invention relates to the provision of checkpoint inhibitors in conjunction with BCG treatments and statin treatments, especially when the BCG has been modified to express p53 and/or tomatidine. As the immune system is critically involved in the development, structural nature and progression of certain cancers, an inflammatory environment is believed to be related to tumor development. Chronic inflammation occurs due to tumor environment stress and the tumor microenvironment resembles an inflammation site, with metastatic sites creating a cytokine milieu conducive to tumor growth. In particular embodiments of the present invention, controlling cytokines is desired at particular sites of an individual's body, rather than systemic control of cytokines. Cytokines of the TNF family regulate a wide range of different immune defense mechanisms, both of the innate and the adaptive types. However, when acting in excess, they can cause significant damage. The ligands of the TNF family are cell-bound transmembrane proteins and thus exert their effects largely by affecting only cells that are located adjacently to the ligand-producing cell. Selective suppression of the ligand producing cells in situations where the ligand plays a pathogenic role forms one aspect of various embodiments of the present invention, such as where destruction of cells producing a cytokine may be preferable over mere attempts to achieve direct blocking of the function of the cytokine molecules. Destruction of cytokine-producing cells prevents further synthesis of the cytokines and provides durable protection. Blocking circulating cytokines affects the whole body. Destruction of cytokine-producing cells, in contrast, may be restricted to a particular site in the body while maintaining beneficial effects of the cytokine at other sites. Using the methods and systems as described herein, the direct and local administration of agents, such as p53, statins, tomatidine, rapamycin, etc. can be employed to achieve the desired non-systemic administration of such agents to tissues.

In certain embodiments of the present invention, the focus is to interfere with the ribosomes of cells being compelled to translate tumor related mRNAs. A ribosome translation factor eIF2 is produced in normal cells. In cancerous cells, however, a different translational factor is transcribed: eIF2A. Employing the use of eIF2A to transcribe certain proteins, such as tomatidine, statins, rapamycin and/or p53, forms yet another aspect of the present invention.

Bacteria in human microbiomes may be genetically modified or replaced without risking cancer or immune rejection. The present invention offers a new medicinal paradigm focused on immunizing microbes against pathogenesis and harnessing them as living therapeutics. In various embodiments, stable populations of engineered cells secrete consistent levels of therapeutic and regulatory molecules for the in situ treatment of disease, and in particular, cancer and cachexia. CRISPR-Cas systems are effective in achieving such purposes.

In certain embodiments, the invention is directed to a method of treating cancer cachexia in an individual in need of such treatment by administering a therapeutically effective amount of a composition comprising *bacillus* calmette-guerin adapted to produce tomatidine. In certain embodiments, the cancer is bladder cancer. In others it is colorectal cancer. Preferably, the *bacillus* calmette-guerin is modified via a clustered regularly interspaced short palindromic repeats (CRISPR) CRISPR associated protein (Cas) system to produce tomatidine, and even more preferably comprises a CRISPR-Cas9 (clustered regularly interspaced short palindromic repeats—CRISPR-associated 9). Other embodiments are directed to the use of *bacillus* calmette-guerin adapted to produce rapamycin. Rapamycin is an immunosuppressant drug used to prevent activation of T cells and B cells by inhibiting their response to interleukin-2 (IL-2). Its mode of action is to bind the cytosolic protein FK-binding protein 12 (FKBP12), and the sirolimus-FKBP12 complex in turn inhibits the mammalian target of sirolimus (mTOR) pathway by directly binding the mTOR Complex1 (mTORC1).

Still other embodiments of the present invention are directed to use of *bacillus* calmette-guerin adapted to produce neoalbaconol. Some embodiments are directed to the use of *bacillus* calmette-guerin adapted to produce p53 having a stable tetrameric structure, preferably with at least one other foreign gene expressed that has anti-cancer characteristics. In various embodiments, the cancer being treated is a metastatic cancer. In still other embodiments, another tumor suppressor is employed, and in a specific embodiment, the tumor suppressor phosphatase and tensin homolog (PTEN) is employed, especially in concert with tomatidine, statin and/or p53 generating embodiments as described herein.

While p53 is a tumor suppressor gene with an established role in the majority of human neoplasias, its homologues—p63 and p73, cannot be classified as tumor suppressors, since they encode isoforms with oncogenic properties as well. p63 plays a crucial role in epithelial cell differentiation and p73 is essential for neuronal cell development. The p63 and p73 expressions have been investigated in a variety of human tumors including bladder carcinomas. The mRNA expression of p53, p63 and p73 in bladder tumors are up-regulated in malignant specimens. High levels of p63 correlate with non-muscle invasive tumors with frequent relapses, whereas p73 overexpression is associated with a more aggressive tumor phenotype. Certain aspects of the present invention involve the ability to enhance the quantity and with respect to p53, the quality (e.g. in terms of competently folded p53) such that appropriate and desired levels of the production of p53 by a person's microbiome may be employed to assist in regulating the amount of p53 for the treatment of various cancers at various different stages of cancer development.

The effectiveness of BCG therapy is believed to be determined by the presence of specific genetic mutations within cancer cells. The BCG pathogen invades the cancer cells and—once inside—leads to their destruction. BCG is a *mycobacterium*, a type of bacteria taken in only by certain immune cells that are looking for invaders to destroy. Cancer cells with mutations in the gene PTEN are highly susceptible to mycobacterial infection. The PTEN protein normally acts as a tumor suppressor; impaired PTEN function appears to increase a cell's vulnerability to becoming cancerous and also to mycobacterial infection. Mutations in PTEN are known to be involved in the onset of bladder cancer. Such cells readily take up BCG via a pathway different from the one BCG usually employs to enter immune cells. One aspect of the present invention is directed to the purposeful employment of mutating PTEN so as to permit BCG to enter cells that would otherwise not permit BCG to enter. RNA-guided Cas9 nuclease can be used to include such mutations in cells. This counter-intuitive method is therefore directed to employing PTEN to permit BCG that has been adapted to express one of tomatidine and/or p53, such that the human cells permit such transformed BCG to enter and to then allow treatments to such cells to preclude cancer progression. In other words, in certain embodiments, BCG cells are either both adapted to produce PTEN and enhanced levels of p53 and/or tomatidine, such that such cells are taken up by human cells, or separate BCG cells are individually transformed with one of PTEN, p53 or tomatidine such that when such cells are provided in combination to a patient, the desired uptake of cells making p53 and/or tomatidine is achieved.

Another aspect of the present invention is directed to the employment of statins to ameliorate the negative impacts of mutated p53 proteins experienced in individuals with cancer. Statins, such as Lipitor (atorvastatin), Crestor (rosuvastatin) and Mevacor (lovastatin) are therefore employed to shut down structurally mutated p53 proteins that can accelerate cancer progression. Such statins, however are not believed to affect competently folded p53 proteins or the genes that produce the same. Thus, statins, as well as other agents that are adapted and able to neutralize mutated p53 proteins is one feature of various embodiments of the present invention. Statins have epigenetic modulating adjuvant activities, thereby epigenetically altering the regulation of expression of genes in chromosomes. Specifically, statins inhibit histone lysine specific demethylase 1 (LSD1) and/or and a histone lysine specific demethylase 2 (LSD2). Statins are compounds of natural origin that are biosynthesized as secondary metabolites of several filamentous fungi and act as competitive inhibitors of HMG-CoA reductase.

They are bulky and literally get "stuck" in the active site. This prevents the enzyme from binding with its substrate, HMG-CoA. There are two classes of statins: Natural Statins: Lovastatin (Mevacor™), Compactin, Pravastatin (Pravachol™), Simvastatin (Zocor™) and Synthetic Statins: Atorvastatin (Lipitor) and Fluvastatin (Lescol). The most common statins are atorvastatin (Lipitor™), fluvastatin (Lescol™), lovastatin (Mevacor™, Altocor™), pravastatin (Pravachol™), simvastatin (Zocor™), and rosuvastatin (Crestor™).

Statins are the treatment of choice for the management of hypercholesterolaemia because of their proven efficacy and safety profile and they can exert antiatherosclerotic effects independently of their hypolipidemic action. Lovastatin basically improves the endothelial function, modulates inflammatory responses, maintain plaque stability and prevent thrombus formation, with which all sorts artery related diseases could be cured and it has been suggested that the consequence of the shrinkage of the lipid core of the atherosclerotic plaque, avoiding plaque rupture that would otherwise trigger intramural hemorrhage and intraluminal thrombosis. Statins, in addition to their lipid lowering effects, have anti-inflammatory and immunomodulatory properties. These properties of statins have suggested that they could have beneficial effects in immune mediated neurological disorders. Lovastatin is also used for the inhibition of the induction of inducible nitric oxide synthase and proinflammatory cytokines. Certain embodiments of the present invention involve the inclusion of genes that code for statins and that are expressed in bacterial cells that are provided to an individual's microbiome. CRISPR-Cas systems, including but not limited to Cas9 and CasX can be employed for this purpose.

Mutant forms of p53 have been found in nearly half of all malignant tumors and nearly every type of human cancer. When p53 works properly, it keeps cells from growing and dividing too quickly. When p53 becomes mutated, cells can grow out of control, forming tumors and invading normal tissues. Mutant p53 is believed to further accelerate the progression of cancer and may also be involved in drug resistance. It is believed that statins work only on structurally mutated (misfolded) p53, as opposed to p53 mutated at the spot where it binds to DNA. While not bound by theory, statins are believed to degrade mutant p53. Because mutant p53 is not usually present in normal cells, all this happens without affecting healthy cells. Thus, in combination with the methods as described herein, the use of statins or other p53-degrading drugs is a viable way to treat cancer and thus, cancer cachexia. Mutant p53 makes human cancer cells more metastatic and resistant to chemotherapy.

In certain embodiments of the present invention, the co-administration of statins (in concert with beg treatments as adapted as described herein, e.g. to express particular agents/proteins, such as tomatidine and/or p53) is believed to be effective in neutralizing mutant p53 proteins in an individual. Thus, certain embodiments involve a method and system that permits competently folded p53 to be present to keep cancer progression in check, as well as to otherwise reduce the pro-cancer activities of mutant p53 via the administration of statins, which are believed to thwart the mutant p53 pro-cancer activities. In still other embodiments, adapting an individual's microbiome to produce desired amounts of statins, particularly in concert with other cells adapted to produce p53 and/or tomatidine, is one way in which to treat cancer, with competently folded p53 levels increasing and misfolded or otherwise muted p53 proteins being reduced in number, thus stopping the cancerous growth of cells. In various embodiments of the present invention, the use of statins, such as Lipitor™ (atorvastatin), Crestor™ (rosuvastatin) and Mevacor™ (lovastatin), may be used to shut down structurally mutated p53 proteins that can accelerate cancer progression, while not harming proteins produced by healthy p53 genes.

Various aspects of the present invention employ the co-administration of statins, such as Lipitor™ (atorvastatin), Crestor™ (rosuvastatin) and Mevacor™ (lovastatin). It is believed that such statins can shut down structurally mutated p53 proteins that can accelerate cancer progression, while not harming proteins produced by healthy p53 genes. Administration of statins is preferably via cells of an individual's microbiome, but may otherwise be administered systemically as in orally, etc. While bound by theory, it is believed that statins preferentially suppress mutp53-expressing cancer cell growth. Specific reduction of mevalonate-5-phosphate by statins or mevalonate kinase knockdown induces CHIP ubiquitin ligase-mediated nuclear export, ubiquitylation, and degradation of mutp53 by impairing interaction of mutp53 with DNAJA1, a Hsp40 family.

Certain embodiments involve the production of statins by microbes that exist or may be added to an individual's microbiome. In embodiments using bacteria, it is possible to transfer of the metabolic pathway for statins to one or more bacterial species. Thus, a prokaryotic host cell can be used, examples of which are, but are not limited to, *Streptomyces* species (i.e. *Streptomyces carbophilus, Streptomyces flavidovirens, Streptomyces coelicolor, Streptomyces lividans, Streptomyces exfoliatus*) or *Amycolatopsis* species (i.e. *Amycolatopsis orientalisor Bacillus* species (i.e. *Bacillus subtilus, Bacillus amyloliquefaciens, Bacillus licheniformis*) or *Corynebacterium* species (i.e. *Corynebacterium glutamicum*) or *Escherichia* species (i.e. *Escherichia coli*).

A significant limitation of current BCG treatment is the lack of response in a substantial number of patients. For example, depending on the endpoint studied, up to 50% of patients fail to respond and show progression of the cancer to muscle invasive disease. Approximately one-third of patients that initially respond to therapy show tumor recurrence. Patients with no measurable pre-existing T-cell immunity to BCG (due to previous BCG immunization or natural exposure to mycobacteria) have a lower recurrence-free survival rate. It is also known that BCG immunotherapy in some patients has severe side effects resulting from local or systemic infection with BCG. High-grade muscle invasive disease is typically treated with radical cystectomy or a combination of radiation therapy and chemotherapy. However, even after treatment the tumor usually remains and patients are at risk of tumor progression, leading to a shortened life expectancy or death from metastatic disease. Immune system cell subsets that have potential roles in BCG therapy include CD4+ and CD8+ lymphocytes, natural killer cells, granulocytes, macrophages, and dendritic cells. Bladder cancer cells are killed through direct cytotoxicity by these cells, by secretion of soluble factors such as TRAIL (tumor necrosis factor-related apoptosis-inducing ligand), and, to some degree, by the direct action of BCG. The use of BCG in the treatment of bladder cancer has BCG functioning as a TLR agonist. In particular, TLR2 and TLR4 appear to regulate distinct aspects of the host immune response against BCG. Aspects of the present invention are directed toward the modification of an individual's microbiome such that BCG is employed to treat their cancer, for example bladder or colorectal cancer, with such modified microbiome cells adapted to express competently folded p53, with either the same cells or other BCG modified cells, expressing tomatidine. In a more general context, the employment of an individual's immune system is believed to be a promising approach for the treatment of cancer because of its potential to specifically target tumor cells while limiting harm to normal tissue, with durability of benefit associated with immunologic memory.

While not bound by theory, it is believed that mutant p53 loses its wild-type tumor suppressive functions and acquires oncogenic properties and can therefore promote skeletal muscle atrophy. There is also evidence that mutated p53 is also involved in diverse muscle atrophy stimuli (muscle unloading, muscle denervation, aging, and Huntington's Disease.) In contrast, competently folded or non-mutated p53 fights cancer by causing damaged cells to die or by halting the growth of mutant cells before they become cancerous and spread to the rest of the body. It is believed that p53 mediates the ATF4-independent pathway to skeletal muscle atrophy. So one aspect of the present invention relates to the ability to employ the microbiome of an individual to adjust the amounts of competently folded, non-mutated p53, and to limit the production (or by the use of other expressed factors or administered factors, such as statins, to ameliorate the effect of mutated p53 proteins) so as to deter the increased levels of mutated p53 from advancing cancer, while promoting the production of competent p53 to control the growth and progression of cancer. In preferred embodiments, this is achieved by the production of p53 by bacteria provided to an individual's microbiome.

More than 50% of all human cancers carry defects in the p53 gene, and almost all other cancers with a normal p53 function carry other defects which indirectly impair the cancer-fighting function of p53. The integrity of p53 affects the production of a special cell surface protein called Major Histocompatibility Complex (MHC) class I. MHC class I molecules on the cancer cell surface serve as targets for the immune system. Therefore, having less MHC I molecules may allow cancer cells to hide better and escape detection by the immune system. p53 moderates the expression of MHC I by controlling the amount of another protein called ERAP1 in the cells. A number of disease conditions including tumor malignancy, multiple sclerosis and autoimmune disease are reported to be associated with ERAP1. Thus, certain embodiments of the present invention are directed to the production of ERAP1 and MHC1, by for example bacteria (e.g. BCG) that have been modified and administered to an individual to facilitate the treatment of cancer, in combination with the provision of microbiome generated products, such as competently folded p53, tomatidine, PTEN, etc.

The claimed method has application in treating an admittedly wide scope of cancers, and encompasses certain embodiments where the administration of tomatidine, statins, rapamycin and p53 is by way of an individual's microbiome and (at least in some embodiments) employ bacteria that have been modified by employing CRISPR-Cas systems to arrive at bacteria able to express desired amounts of tomatidine and p53. Moreover, it is now known that p53 activates genes involved in the production of reactive oxygen species, which promote mitochondrial sensitization to proapoptotic effects. Apart from its effects on transcription, p53 directly induces cell death by interacting with mitochondrial components. While cells of different histogenetic lineages utilize different mechanisms of apoptosis, the inductor roll is always played by a single protein—p53. Cancer cells acquire a higher sensitivity to exogenous p53 such that when wild-type p53 are introduced in cancer cells, they exert a massive suppressor effect, inducing apoptosis. Even when only a minor portion of tumor cells include the provision of competently folded p53, a substantial therapeutic effect is observed, believed to be due to cell-to-cell contacts, certain secreted factors, etc. One of ordinary skill in the art will appreciate that various bacteria are able to target the nucleus of eukaryotic cells and thus, the provision of p53 and/or tomatidine inside a cell nucleus is entirely within the skill of one of ordinary skill in the art.

The use of CRISPR/Cas 9 systems are now available to one of ordinary skill in the art to make relatively large DNA fragment insertions, including an insertion of a gene of about 65 kb in size and the methods are technically easy, time saving and cost effective. As the p53 gene is approximately 20 kb it is clear that one of ordinary skill in the art is able to bacterially express p53 proteins in the microbiota of an individual. It is known that p53 activates genes involved in the production and excretion of large amounts of reactive oxygen species, which promotes mitochondrial sensitization to proapoptotic effects. Thus, in addition to its effects on transcription, p53 directly induces cell death by interacting with mitochondrial components to achieve proapoptotic effects. It is not the case, therefore, that p53 anti-cancer activity is entirely dependent upon crossing the nuclear membrane. With mutations within the p53 gene being the most common acquired cancer-driving genetic change, some researchers refer to reactivating p53 responses to kill cancer cells as being the "holy grail" of oncology. There is substantial cross-talk between microbiota and the immune system that can lead to inflammation and it is therefore believed that the immune response can mitigate carcinogenesis. More than half of all human cancers carry mutations in the p53 gene. Many of these mutations don't simply disrupt the normal function of p53, they also endow p53 with new functions that promote, instead of inhibit, cancer formation.

Various embodiments of the present claimed invention are directed to an approach in the treatment of cachexia that modifies an individual's microbiome to provide effective amounts of tomatidine/p53 to therapeutically address muscle wasting that attends various types of cancer. In other words, the cachexia causing cellular pathway involved in a variety of cancers is one target of the present invention. It is now appreciated that cachexia is not merely a complication of tumor progression and that it does not correspond to tumor mass. Numerous bacteria that inhabit the human microbiota are listed and described in the specification. The provision of a therapeutically effective dose is well within the skill of one of ordinary skill in the art, especially in view of recent human studies that involve the use of tomatidine to address skeletal muscle atrophy. U.S. Pat. No. 9,254,295 to Dyle et al. is incorporated herein by this reference. Provision of agents such as tomatidine and p53 by bacterial cells of the microbiome is something that can be accomplished by one of ordinary skill in the art with the guidance provided by the present specification, especially in view of the extensive materials that are incorporated by reference and that further provide various details, procedures, etc. to accomplish the varied ways such bacterial modification of bacteria can produce therapeutic amounts of tomatidine and p53. Large molecules—which have a molecular weight greater than 5000 Daltons—move mainly by convection. Tomatidine has a molecular weight of 415 Daltons and thus, can be effectively delivered to solid tumor masses. Having tomatidine provided to an individual via that person's microbiome is believed to alleviate the repeated dosing problems experienced in other drug delivery regimens. Similarly, p53 is not a large protein and thus, is capable of being administered to cells in an effective manner by employing the methods as suggested herein.

The present inventors believe that there are various indications that suggest that p53 is key to the treatment of cancer. For example, elephants are about 100 times the size of people and thus have 100 times as many cells dividing decade after decade. Elephants live 50, 60, 70 years. But elephants do not get cancer in proportion to their body mass because they produce many times as much p53 as do humans. Humans have two copies of p53, while elephants have 40 copies. Thus, this supports one of the basic tenants of the present invention: that production of competently folded p53 protein is effective in defeating cancer progression. Certain aspects of the present invention are directed to a method for treating cancer in a subject comprising administering to a subject in need thereof a therapeutically effective amount of a statin in combination with bcg adapted to express one of p53 and tomatidine.

The cytoplasmic polyadenylation element-binding (CPEB) proteins regulate pre-mRNA processing and translation of CPE-containing mRNAs in early embryonic development and synaptic activity. CPEB4 is essential to drive the liver's response to stress. The protein allows the cell to 'clean-up' the excess fat. Without CPEB4, the endoplasmic reticulum is unable to activate the stress response, thus causing hepatocytes to accumulate the lipids produced by the fatty liver. CPEB4 is required for adaptation to high-fat-diet- and ageing-induced endoplasmic reticulum (ER) stress, and subsequent hepatosteatosis. CPEB4 deficiency results in non-alcoholic fatty liver disease. One aspect of the present invention is directed to the expression of CPEB protein by an individual's microbiome. The purposeful provision of CPEB protein by bacteria that are modified via the CRISPR-Cas system to express such protein is one aspect of the present invention, directed to the treatment of NAFLD.

Still other aspects of the present invention are directed to the involvement with cholesterol drugs in the control of cancer. As discussed herein the use of statins may not only affect cholesterol levels, but are believed to be effective in ameliorating certain adverse effects stemming from mutant p53 on cancer progression. The employment of other anti-cholesterol drugs, such as, for example, repatha, offered by Amgen, and Praluent, both of which have shown an ability to reduce "bad" cholesterol levels in patients may be employed, in combination or in pace of statins, to achieve the regulation of mutant p53 effects. Production of such anti-cholesterol drugs by bacteria in an individual's microbiome, is one aspect of the present invention. Incorporated herein by this reference are the following to provide written description and enablement for such embodiments: U.S. Pat. Nos. 8,829,165; 8,859,741; 8,030,457 and 9,045,547. Still other embodiments include the provision to an individual's microbiome of the human-engineered protein pegfilgrastim, to stimulate the production of neutrophils and to decrease the incidence of infection.

Various aspects of the present invention are directed towards the use of herbal compounds with anti-cancer effects and the provision of genes for such compounds in microbes, preferably bacteria that is able to be maintained in an individual's microbiome, such that such compounds can be produced in a manner effective to treat disease, including cancer. For example, the expression of genes for statin compounds within microbes of an individual's microbiome (e.g. via the employment of CRISPR-Cas systems) provides a way for beneficial anti-cancer treatments to be used, especially in combination with other aspects of the present invention, such as production of p53 and/or tomatidine by still other microbes in the person's microbiome. It is now appreciated that stabilization of mutant p53 (mutp53) in tumors greatly contributes to malignant progression. While little is known about the underlying mechanisms and therapeutic approaches to destabilize mutp53, the present inventors believe that the use of statins, cholesterol-lowering drugs, may be used as degradation inducers for conformational or misfolded p53 mutants with minimal effects on wild-type p53 (wtp53). Statins preferentially suppress mutp53-expressing cancer cell growth. Specific reduction of mevalonate-5-phosphate by statins or mevalonate kinase knockdown induces CHIP ubiquitin ligase-mediated nuclear export, ubiquitylation, and degradation of mutp53 by impairing interaction of mutp53 with DNAJA1, a Hsp40 family member. Thus, in preferred embodiments, administration of statins to those suffering from cancer, in concert with administration of tomatidine and wild type p53 is believed to be effective in the treatment of various forms of cancer. While wild-type p53 expression is important in the ability to thwart cancer progression, mutant forms of the p53 tumor suppressor are now known to acquire pro-oncogenic activities. Therefore, inhibition of the mevalonate pathway can promote degradation of select oncogenic mutant p53 proteins, such that the destabilization of mutant p53, especially in concert with the provision of wild type p53 to an individual, preferably via expression by microbes in the person's microbiome, is an effective cancer therapy.

Enhanced proliferation and survival are common features of cancer cells. Cancer cells are metabolically reprogrammed which aids in their survival in nutrient-poor environments. Changes in metabolism of glucose and glutamine are essential for tumor progression. Metabolic reprogramming is a hallmark of cancer and in particular, the reprogramming of lipid metabolism in cancer cells permits cancer to progress by providing lipids used for biosynthesis of membranes, post-translational modifications, second messengers for signal transduction, and as a source of energy during nutrient deprivation. The tumor suppressor p53 is a transcription factor that controls the expression of proteins involved in cell cycle arrest, DNA repair, apoptosis, and senescence. p53 also regulates cellular metabolism and plays a key role in tumor suppressive activities. Conversely, mutant p53 contributes to cancer progression through the upregulation of cholesterol production and protein prenylation. As statins act by competitively inhibiting the enzyme HMG-CoA reductase, the first committed enzyme of the mevalonate pathway, due to the similar structure of statins and HMG-CoA on a molecular level, they fit into the enzyme's active site and compete with the native substrate (HMG-CoA). This competition reduces the rate by which HMG-CoA reductase is able to produce mevalonate, the next molecule in the cascade that eventually produces cholesterol. By inhibiting HMG-CoA reductase, statins block the pathway for synthesizing cholesterol in the liver.

The present invention in various embodiments is devoid of significant amounts of ursolic acid and in preferred embodiments, the amount of tomatidine produced is greater than the amount of ursolic acid produced, e.g. by the bacteria employed, such as BCG. Although ursolic acid reportedly benefits muscle protein metabolism, the compound is believed to also exert undesired cytotoxic effects on cells. Some have observed that low concentrations ursolic acid (1 to 5 µM) increased the rate of protein synthesis in myotubes in a dose-dependent fashion. At higher concentrations (>10 µM), ursolic acid blocked protein synthesis. While not bound by theory, ursolic acid increases muscle proteolysis by stimulating E3 ubiquitin ligases but also suppresses myostatin to activate protein synthesis. Ursolic acid can directly act to suppress myostatin transcription rather than via pathways such as IGF/insulin/Akt signaling. Levels of phosphorylation of NF-kB and STAT3 and p38 are significantly suppressed by ursolic acid, indicating that there is an anti-inflammatory property of ursolic acid and this could improve the cachexia. Thus, in certain embodiments, both tomatidine and ursolic acid production by an individual's microbiome is employed to exert anti-cachexia effects, via at least one of the following: suppression of myostatin, inhibition of inflammatory responses; and enhancement of IGF-1/insulin/Akt signaling.

Tomatidine, and its glycosides α-, β-, γ-, and δ-tomatine are mainly found in the stems, leaves, and fruits of tomato plants. Tomatidine can arrest cancer cells in G0/G1 cell cycle phase. While not bound by theory, it is believed that tomatidine chemosensitizes cancer cells, and thus, its use as described herein may further be employed in combination with chemotherapeutic drugs to treat cancer. In certain embodiments, the addition of a carbohydrate moiety may be used to enhance the cytotoxicity of tomatidine.

In some embodiments, methods further comprise administering to the subject an immune checkpoint inhibitor via cells within an individual's microbiome. Use of CRISPR-Cas systems to modify desired bacteria or other microbes to produce desired amounts of such inhibitors is thus one aspect of the preset invention. In some embodiments, the immune checkpoint inhibitor is a protein or polypeptide that specifically binds to an immune checkpoint protein. In some embodiments, the immune checkpoint protein is selected from the group consisting of CTLA4, PD-1, PD-L1, PD-L2, A2AR, B7-H3, B7-H4, BTLA, KIR, LAG3, TIM-3 or VISTA. In some embodiments, the polypeptide or protein is an antibody or antigen-binding fragment thereof. In some embodiments, the immune checkpoint inhibitor is an interfering nucleic acid molecule. In some embodiments, the interfering nucleic acid molecule is an siRNA molecule, an shRNA molecule or an antisense RNA molecule. In some embodiments, the immune checkpoint inhibitor is selected from the group consisting of nivolumab, pembrolizumab, pidilizumab, AMP-224, AMP-514, STI-A1110, TSR-042, RG-7446, BMS-936559, BMS-936558, MK-3475, CT O11, MPDL3280A, MEDI-4736, MSB-0020718C, AUR-012 and STI-A1010. In some embodiments, the immune checkpoint inhibitor is administered before the bacterial formulation. In some embodiments, the immune checkpoint inhibitor is administered at least one day before the bacterial formulation. In some embodiments, the immune checkpoint is administered at about the same time as the bacterial formulation. In some embodiments, the immune checkpoint inhibitor is administered on the same day as the bacterial formulation. In some embodiments, the immune checkpoint inhibitor is administered after the bacterial formulation. In some embodiments, the immune checkpoint inhibitor is administered at least one day after the bacterial formulation. In some embodiments, the immune checkpoint inhibitor is administered by injection. In some embodiments, the injection is an intravenous, intramuscular, intratumoral or subcutaneous injection.

Therefore, in some embodiments, the invention is directed to a system and method of treating cancer in a human subject comprising administering to the subject an immune checkpoint inhibitor via the expression thereof by an individual's microbiome, and includes, for example, expression using bacteria of the genera *Bifidobacterium*. Using CRISPR-Cas systems, one is able to achieve expression of genes and gene products in prokaryotic cells that provide desired amounts of checkpoint inhibitors to a person so as to effectively treat various forms of cancer. In such a manner, aspects of the present invention take advantage of the commensal relationship between the human host and the microbiome for the targeted delivery of nucleic acid therapies. In certain embodiments, employing the methods set forth herein one is able to deliver nucleic acids to program bacteria for expression of therapeutic proteins and RNA molecules in vivo at sites of greatest significance for a particular disease, thus providing for higher local concentrations of therapeutic products while reducing off-target effects.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention. Those skilled in the art will appreciate that the conception upon which this disclosure is based, may readily be utilized as a basis for designing of other structures, methods and systems for carrying out the several purposes of the present invention. It is important, therefore, that the claims be regarded as including any such equivalent construction insofar as they do not depart from the spirit and scope of the present invention.

What is claimed is:

1. A method of treating cancer cachexia in a subject in need of such treatment, said method comprising a step of administering a therapeutically effective amount of a composition comprising *bacillus* calmette-guerin adapted to produce tomatidine, wherein the cancer is bladder cancer; and
    wherein the *bacillus* calmette-guerin has been modified via a clustered regularly interspaced short palindromic repeats (CRISPR) CRISPR associated protein (Cas) system to produce tomatidine.

2. A method of treating cancer cachexia in a subject in need of such treatment, said method comprising a step of administering a therapeutically effective amount of a composition comprising *bacillus* calmette-guerin adapted to produce tomatidine, wherein the cancer is bladder cancer; and
    wherein the *bacillus* calmette-guerin is further adapted to produce rapamycin.

3. A method of treating cancer cachexia in a subject in need of such treatment, said method comprising a step of administering a therapeutically effective amount of a composition comprising *bacillus* calmette-guerin adapted to produce tomatidine, wherein the cancer is bladder cancer; and
    wherein the *bacillus* calmette-guerin is further adapted to produce p53.

4. A method of treating cancer cachexia in a subject in need of such treatment, said method comprising a step of administering a therapeutically effective amount of a composition comprising *bacillus* calmette-guerin adapted to produce tomatidine, wherein the cancer is colorectal cancer; and
    wherein the *bacillus* calmette-guerin is further adapted to produce rapamycin.

5. A method of treating cancer cachexia in a subject in need of such treatment, said method comprising a step of administering a therapeutically effective amount of a composition comprising *bacillus* calmette-guerin adapted to produce tomatidine, wherein the cancer is colorectal cancer; and
    wherein the *bacillus* calmette-guerin is further adapted to produce p53.

6. A method of treating cancer cachexia in a subject in need of such treatment, said method comprising a step of administering a therapeutically effective amount of a microbial composition comprising *bacillus* calmette-guerin adapted to produce p53 and rapamycin; and
    wherein the composition has been modified to express tomatidine.

7. A method of treating cancer cachexia in a subject in need of such treatment, said method comprising a step of administering a therapeutically effective amount of a microbial composition comprising *bacillus* calmette-guerin adapted to produce p53 and rapamycin; and
    wherein the composition further comprises phosphatase and tensin homolog (PTEN).

* * * * *